(12) United States Patent
Pimenta et al.

(10) Patent No.: US 9,757,246 B1
(45) Date of Patent: Sep. 12, 2017

(54) METHODS AND APPARATUS FOR PERFORMING SPINE SURGERY

(71) Applicant: NuVasive, Inc., San Diego, CA (US)

(72) Inventors: Luiz Pimenta, Sao Paulo (BR);
Andrew Morris, San Diego, CA (US);
Brian Snider, San Diego, CA (US);
Michael Serra, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 14/918,137

(22) Filed: Oct. 20, 2015

Related U.S. Application Data

(63) Continuation of application No. 14/578,215, filed on Dec. 19, 2014, now Pat. No. 9,192,482, which is a continuation of application No. 13/653,335, filed on Oct. 16, 2012, now Pat. No. 8,920,500, which is a continuation of application No. 12/799,021, filed on Apr. 16, 2010, now Pat. No. 8,287,597.

(60) Provisional application No. 61/319,823, filed on Mar. 31, 2010, provisional application No. 61/212,921, filed on Apr. 16, 2009.

(51) Int. Cl.
*A61F 2/44* (2006.01)
*A61F 2/30* (2006.01)

(52) U.S. Cl.
CPC .... *A61F 2/442* (2013.01); *A61F 2002/30176* (2013.01); *A61F 2002/30433* (2013.01); *A61F 2002/30772* (2013.01); *A61F 2002/30828* (2013.01); *A61F 2002/444* (2013.01)

(58) Field of Classification Search
CPC ...... A61F 2/4611; A61F 2/447; A61F 2/4455; A61F 2002/4475; A61F 2/44; A61F 2002/30281; A61F 2/46

USPC ........................................... 623/17.11–17.16
See application file for complete search history.

(56) References Cited

U.S. PATENT DOCUMENTS

| | | | |
|---|---|---|---|
| 208,227 A | 9/1878 | Dorr |
| 972,983 A | 10/1910 | Arthur |
| 1,328,624 A | 1/1920 | Graham |
| 1,548,184 A | 8/1925 | Cameron |
| 2,704,064 A | 6/1955 | Fizzell et al. |
| 2,736,002 A | 2/1956 | Oriel |
| 2,808,826 A | 10/1957 | Reiner et al. |
| 3,364,929 A | 1/1968 | Ide et al. |
| 3,486,505 A | 12/1969 | Morrison |

(Continued)

FOREIGN PATENT DOCUMENTS

| CA | 2015507 | 1/1999 |
|---|---|---|
| DE | 299 08 259 | 7/1999 |

(Continued)

OTHER PUBLICATIONS

Anatomy of the Lumbar Spine in MED TM MicroEndoscopic Discectomy (1997 Ludann Grand Rapids MI), 14 pgs.

(Continued)

*Primary Examiner* — Eduardo C Robert
*Assistant Examiner* — Michelle C Eckman
(74) *Attorney, Agent, or Firm* — Bradley Arant Boult Cummings

(57) ABSTRACT

Systems and methods are described for correcting sagittal imbalance in a spine including instruments for performing the controlled release of the anterior longitudinal ligament through a lateral access corridor and hyper-lordotic lateral implants.

21 Claims, 7 Drawing Sheets

(56) References Cited

U.S. PATENT DOCUMENTS

| | | |
|---|---|---|
| 3,518,993 A | 7/1970 | Blake |
| 3,604,487 A | 9/1971 | Gilbert |
| 3,664,329 A | 5/1972 | Naylor |
| 3,682,162 A | 8/1972 | Colyer |
| 3,745,995 A | 7/1973 | Kraus |
| 3,785,368 A | 1/1974 | McCarthy et al. |
| 3,830,226 A | 8/1974 | Staub et al. |
| 3,848,601 A | 11/1974 | Ma et al. |
| 3,867,728 A | 2/1975 | Stubstad et al. |
| 3,957,036 A | 5/1976 | Normann |
| 4,026,304 A | 5/1977 | Levy |
| 4,026,305 A | 5/1977 | Brownlee et al. |
| 4,099,519 A | 7/1978 | Warren |
| 4,164,214 A | 8/1979 | Stark et al. |
| 4,207,897 A | 6/1980 | Lloyd et al. |
| 4,224,949 A | 9/1980 | Scott et al. |
| 4,226,228 A | 10/1980 | Shin et al. |
| 4,235,242 A | 11/1980 | Howson et al. |
| 4,285,347 A | 8/1981 | Hess |
| 4,291,705 A | 9/1981 | Severinghaus et al. |
| 4,461,300 A | 7/1984 | Christensen |
| 4,501,269 A | 2/1985 | Bagby |
| 4,515,168 A | 5/1985 | Chester et al. |
| 4,519,403 A | 5/1985 | Dickhudt |
| 4,545,374 A | 10/1985 | Jacobson |
| 4,561,445 A | 12/1985 | Berke et al. |
| 4,562,832 A | 1/1986 | Wilder et al. |
| 4,573,448 A | 3/1986 | Kambin |
| 4,592,369 A | 6/1986 | Davis et al. |
| 4,595,018 A | 6/1986 | Rantala |
| 4,611,597 A | 9/1986 | Kraus |
| 4,633,889 A | 1/1987 | Talalla |
| 4,646,738 A | 3/1987 | Trott |
| 4,657,550 A | 4/1987 | Daher |
| 4,658,835 A | 4/1987 | Pohndorf |
| 4,743,256 A | 5/1988 | Brantigan |
| 4,744,371 A | 5/1988 | Harris |
| 4,759,377 A | 7/1988 | Dykstra |
| 4,781,591 A | 11/1988 | Allen |
| 4,784,150 A | 11/1988 | Voorhies et al. |
| 4,807,642 A | 2/1989 | Brown |
| 4,834,757 A | 5/1989 | Brantigan |
| 4,877,020 A | 10/1989 | Vich |
| 4,878,915 A | 11/1989 | Brantigan |
| 4,892,105 A | 1/1990 | Prass |
| 4,913,134 A | 4/1990 | Luque |
| 4,926,865 A | 5/1990 | Oman |
| 4,932,975 A | 6/1990 | Main et al. |
| 4,950,296 A | 8/1990 | McIntyre |
| 4,961,740 A | 10/1990 | Ray et al. |
| 4,962,766 A | 10/1990 | Herzon |
| 4,964,411 A | 10/1990 | Johnson et al. |
| 5,007,902 A | 4/1991 | Witt |
| 5,015,247 A | 5/1991 | Michelson |
| 5,026,373 A | 6/1991 | Ray et al. |
| 5,047,055 A | 9/1991 | Bao et al. |
| 5,052,373 A | 10/1991 | Michelson |
| 5,055,104 A | 10/1991 | Ray |
| 5,058,602 A | 10/1991 | Brody |
| 5,062,845 A | 11/1991 | Kuslich et al. |
| 5,071,437 A | 12/1991 | Steffee |
| 5,081,990 A | 1/1992 | Deletis |
| 5,092,344 A | 3/1992 | Lee |
| 5,092,572 A | 3/1992 | Litwak et al. |
| 5,127,403 A | 7/1992 | Brownlee |
| 5,133,717 A | 7/1992 | Chopin |
| 5,133,755 A | 7/1992 | Brekke |
| 5,161,533 A | 11/1992 | Prass et al. |
| 5,171,278 A | 12/1992 | Pisharodi |
| 5,171,279 A | 12/1992 | Mathews |
| 5,192,327 A | 3/1993 | Brantigan |
| 5,195,541 A | 3/1993 | Obenchain |
| 5,196,015 A | 3/1993 | Neubardt |
| 5,217,497 A | 6/1993 | Mehdian |
| RE34,390 E | 9/1993 | Culver |
| 5,255,691 A | 10/1993 | Otten |
| 5,263,953 A | 11/1993 | Bagby |
| 5,269,785 A | 12/1993 | Bonutti |
| 5,282,468 A | 2/1994 | Klepinski |
| 5,284,153 A | 2/1994 | Raymond et al. |
| 5,284,154 A | 2/1994 | Raymond et al. |
| 5,290,494 A | 3/1994 | Coombes et al. |
| 5,295,994 A | 3/1994 | Bonutti |
| 5,299,563 A | 4/1994 | Seton |
| 5,300,076 A | 4/1994 | Lerich |
| 5,304,210 A | 4/1994 | Crook |
| 5,306,307 A | 4/1994 | Senter et al. |
| 5,306,309 A | 4/1994 | Wagner et al. |
| 5,312,417 A | 5/1994 | Wilk |
| 5,313,956 A | 5/1994 | Knutsson et al. |
| 5,313,962 A | 5/1994 | Obenchain |
| 5,322,505 A | 6/1994 | Krause et al. |
| 5,327,902 A | 7/1994 | Lemmen |
| 5,331,975 A | 7/1994 | Bonutti |
| 5,333,618 A | 8/1994 | Lekhtman et al. |
| 5,334,205 A | 8/1994 | Cain |
| 5,336,223 A | 8/1994 | Rogers |
| 5,342,384 A | 8/1994 | Sugarbaker |
| 5,364,400 A | 11/1994 | Rego, Jr. et al. |
| 5,375,067 A | 12/1994 | Berchin |
| 5,375,594 A | 12/1994 | Cueva |
| 5,383,876 A | 1/1995 | Nardella |
| 5,395,317 A | 3/1995 | Kambin |
| 5,395,372 A | 3/1995 | Holt et al. |
| 5,397,363 A | 3/1995 | Gelbard |
| 5,397,364 A | 3/1995 | Kozak |
| 5,405,391 A | 4/1995 | Hednerson et al. |
| 5,413,602 A | 5/1995 | Metz-Stavenhagen |
| 5,425,772 A * | 6/1995 | Brantigan ............... A61F 2/447 606/247 |
| 5,431,658 A | 7/1995 | Moskovich |
| 5,443,514 A | 8/1995 | Steffee |
| 5,443,515 A * | 8/1995 | Cohen ............... A61F 2/44 606/247 |
| 5,445,639 A | 8/1995 | Kuslich et al. |
| 5,450,845 A | 9/1995 | Axelgaard |
| 5,454,811 A | 10/1995 | Huebner |
| 5,458,638 A * | 10/1995 | Kuslich ............... A61F 2/4455 606/247 |
| 5,458,642 A * | 10/1995 | Beer ............... A61F 2/4425 606/247 |
| 5,474,057 A | 12/1995 | Makower et al. |
| 5,474,558 A | 12/1995 | Neubardt |
| 5,480,440 A | 1/1996 | Kambin |
| 5,482,038 A | 1/1996 | Ruff |
| 5,484,403 A | 1/1996 | Yoakum et al. |
| 5,484,437 A | 1/1996 | Michelson |
| 5,489,307 A | 2/1996 | Kuslich et al. |
| 5,489,308 A | 2/1996 | Kuslich et al. |
| 5,509,893 A | 4/1996 | Pracas |
| 5,514,153 A | 5/1996 | Bonutti |
| 5,514,180 A | 5/1996 | Heggeness et al. |
| 5,522,879 A | 6/1996 | Scopelianos |
| 5,522,899 A | 6/1996 | Michelson |
| 5,524,624 A | 6/1996 | Tepper et al. |
| 5,527,312 A | 6/1996 | Ray |
| 5,534,030 A | 7/1996 | Navarro et al. |
| 5,540,235 A | 7/1996 | Wilson |
| 5,540,688 A | 7/1996 | Navas |
| 5,545,222 A | 8/1996 | Bonutti |
| 5,549,656 A | 8/1996 | Reiss |
| 5,560,372 A | 10/1996 | Cory |
| 5,562,736 A | 10/1996 | Ray et al. |
| 5,565,005 A | 10/1996 | Erickson et al. |
| 5,566,678 A | 10/1996 | Cadwell |
| 5,571,149 A | 11/1996 | Liss et al. |
| 5,571,190 A | 11/1996 | Ulrich |
| 5,571,192 A | 11/1996 | Schonhoffer |
| 5,579,781 A | 12/1996 | Cooke |
| 5,593,409 A | 1/1997 | Michelson |
| 5,593,429 A | 1/1997 | Ruff |
| 5,599,279 A | 2/1997 | Slotman et al. |
| 5,607,424 A * | 3/1997 | Tropiano ............... A61F 2/4455 606/17 |

(56) References Cited

U.S. PATENT DOCUMENTS

| | | |
|---|---|---|
| 5,609,636 A | 3/1997 | Kohrs et al. |
| 5,611,800 A | 3/1997 | Davis et al. |
| 5,611,810 A | 3/1997 | Arnold et al. |
| 5,630,813 A | 5/1997 | Kieturakis |
| 5,632,747 A | 5/1997 | Scarborough et al. |
| 5,645,598 A | 7/1997 | Brosnahan et al. |
| 5,653,761 A | 8/1997 | Pisharodi |
| 5,653,762 A | 8/1997 | Pisharodi |
| 5,658,336 A | 8/1997 | Pisdharodi |
| 5,658,337 A * | 8/1997 | Kohrs ............... A61F 2/447 606/247 |
| 5,662,710 A | 9/1997 | Bonutti |
| 5,665,122 A | 9/1997 | Kambin |
| 5,667,508 A | 9/1997 | Errico et al. |
| 5,669,909 A | 9/1997 | Zdeblick et al. |
| 5,671,752 A | 9/1997 | Sinderby et al. |
| 5,676,703 A | 10/1997 | Gelbard |
| 5,681,265 A | 10/1997 | Maeda et al. |
| 5,683,394 A | 11/1997 | Rinner |
| 5,683,400 A | 11/1997 | McGuire |
| 5,683,464 A | 11/1997 | Wagner et al. |
| 5,690,629 A | 11/1997 | Asher et al. |
| 5,700,264 A | 12/1997 | Zucherman et al. |
| 5,700,291 A | 12/1997 | Kuslich et al. |
| 5,700,292 A | 12/1997 | Margulies |
| 5,702,449 A | 12/1997 | McKay |
| 5,702,451 A | 12/1997 | Biedermann et al. |
| 5,702,453 A | 12/1997 | Rabbe et al. |
| 5,702,454 A | 12/1997 | Baumgartner |
| 5,702,455 A | 12/1997 | Saggar |
| 5,703,451 A | 12/1997 | Yamamichi et al. |
| 5,707,359 A | 1/1998 | Bufalini |
| 5,707,373 A | 1/1998 | Sevrain et al. |
| 5,711,307 A | 1/1998 | Smits |
| 5,711,957 A | 1/1998 | Patat et al. |
| 5,716,415 A | 2/1998 | Steffee |
| 5,720,748 A | 2/1998 | Kuslich et al. |
| 5,720,751 A | 2/1998 | Jackson |
| 5,728,046 A | 3/1998 | Mayer et al. |
| 5,728,159 A | 3/1998 | Stroever et al. |
| 5,741,253 A | 4/1998 | Michelson |
| 5,741,261 A | 4/1998 | Moskovitz et al. |
| 5,755,797 A | 5/1998 | Baumgartner |
| 5,759,159 A | 6/1998 | Masreliez |
| 5,762,629 A | 6/1998 | Kambin |
| 5,766,252 A * | 6/1998 | Henry ............... A61F 2/4455 606/247 |
| 5,772,661 A | 6/1998 | Michelson |
| 5,775,331 A | 7/1998 | Raymond et al. |
| 5,775,797 A | 7/1998 | Henstra |
| 5,776,144 A | 7/1998 | Leysieffer et al. |
| 5,779,642 A | 7/1998 | Nightengale |
| 5,782,830 A | 7/1998 | Farris |
| 5,782,919 A | 7/1998 | Zdeblick et al. |
| 5,785,658 A | 7/1998 | Benaron |
| 5,785,710 A | 7/1998 | Michelson |
| 5,792,044 A | 8/1998 | Foley et al. |
| 5,797,854 A | 8/1998 | Hedgecock |
| 5,797,909 A | 8/1998 | Michelson |
| 5,800,549 A | 9/1998 | Bao et al. |
| 5,800,550 A | 9/1998 | Sertich |
| 5,814,073 A | 9/1998 | Bonutti |
| 5,814,084 A | 9/1998 | Grivas et al. |
| 5,830,151 A | 11/1998 | Hadzic et al. |
| 5,851,191 A | 12/1998 | Gozani |
| 5,851,208 A | 12/1998 | Trott |
| 5,853,373 A | 12/1998 | Griffith et al. |
| 5,860,973 A | 1/1999 | Michelson |
| 5,862,314 A | 1/1999 | Jeddeloh |
| 5,865,845 A | 2/1999 | Thalgott |
| 5,865,848 A | 2/1999 | Baker |
| 5,872,314 A | 2/1999 | Clinton |
| 5,885,210 A | 3/1999 | Cox |
| 5,885,219 A | 3/1999 | Nightengale |
| 5,885,299 A | 3/1999 | Winslow et al. |
| 5,888,196 A | 3/1999 | Bonutti |
| 5,888,219 A | 3/1999 | Bonutti |
| 5,888,224 A * | 3/1999 | Beckers ............... A61F 2/4455 623/17.16 |
| 5,891,147 A | 4/1999 | Moskovitz et al. |
| 5,893,890 A | 4/1999 | Pisharodi |
| 5,902,231 A | 5/1999 | Foley et al. |
| 5,904,719 A * | 5/1999 | Errico ............... A61F 2/446 623/17.16 |
| 5,910,315 A | 6/1999 | Stevenson et al. |
| 5,928,139 A | 7/1999 | Koros et al. |
| 5,928,158 A | 7/1999 | Aristides |
| 5,931,777 A | 8/1999 | Sava |
| 5,935,131 A | 8/1999 | Bonutti et al. |
| 5,938,688 A | 8/1999 | Schiff |
| 5,942,698 A | 8/1999 | Stevens |
| 5,944,658 A | 8/1999 | Koros et al. |
| 5,954,769 A | 9/1999 | Rosenlicht |
| 5,968,098 A | 10/1999 | Winslow |
| 5,976,094 A | 11/1999 | Gozani et al. |
| 5,993,474 A | 11/1999 | Ouchi |
| 6,003,426 A | 12/1999 | Kobayashi et al. |
| 6,004,262 A | 12/1999 | Putz et al. |
| 6,004,312 A | 12/1999 | Finneran |
| 6,004,326 A | 12/1999 | Castro et al. |
| 6,007,487 A | 12/1999 | Foley et al. |
| 6,008,433 A * | 12/1999 | Stone ............... A61B 17/68 623/20.14 |
| 6,015,436 A | 1/2000 | Schunhuffer |
| 6,024,696 A | 2/2000 | Hoftman et al. |
| 6,027,456 A | 2/2000 | Feler et al. |
| 6,033,405 A | 3/2000 | Winslow et al. |
| 6,038,469 A | 3/2000 | Karlsson et al. |
| 6,038,477 A | 3/2000 | Kayyali |
| 6,039,761 A | 3/2000 | Li et al. |
| 6,042,582 A | 3/2000 | Ray |
| 6,045,580 A | 4/2000 | Scarborough et al. |
| 6,048,342 A | 4/2000 | Zucherman et al. |
| 6,050,992 A | 4/2000 | Nichols |
| 6,059,829 A | 5/2000 | Schlapfer et al. |
| 6,063,088 A | 5/2000 | Winslow |
| 6,074,343 A | 6/2000 | Nathanson et al. |
| 6,083,154 A | 7/2000 | Liu et al. |
| 6,083,225 A | 7/2000 | Winslow et al. |
| 6,095,987 A | 8/2000 | Schmulewitz et al. |
| 6,096,080 A | 8/2000 | Nicholson et al. |
| 6,102,948 A | 8/2000 | Brosnahan, III |
| 6,104,957 A | 8/2000 | Alo et al. |
| 6,104,960 A | 8/2000 | Duysens et al. |
| 6,120,503 A | 9/2000 | Michelson |
| 6,120,506 A | 9/2000 | Kohrs et al. |
| 6,126,660 A | 10/2000 | Dietz |
| 6,132,386 A | 10/2000 | Gozani et al. |
| 6,132,387 A | 10/2000 | Gozani et al. |
| 6,132,472 A | 10/2000 | Bonutti |
| 6,135,965 A | 10/2000 | Tumer et al. |
| 6,139,493 A | 10/2000 | Koros et al. |
| 6,143,033 A | 11/2000 | Paul et al. |
| 6,146,335 A | 11/2000 | Gozani |
| 6,152,871 A | 11/2000 | Foley et al. |
| 6,159,211 A | 12/2000 | Boriani et al. |
| 6,159,215 A | 12/2000 | Urbahns et al. |
| 6,161,047 A | 12/2000 | King et al. |
| 6,174,311 B1 | 1/2001 | Branch et al. |
| 6,181,961 B1 | 1/2001 | Prass |
| 6,193,756 B1 | 2/2001 | Studer et al. |
| 6,196,969 B1 | 3/2001 | Bester et al. |
| 6,200,347 B1 | 3/2001 | Anderson |
| 6,206,826 B1 | 3/2001 | Mathews et al. |
| 6,217,509 B1 | 4/2001 | Foley et al. |
| 6,224,549 B1 | 5/2001 | Drongelen |
| 6,224,607 B1 | 5/2001 | Michelson |
| 6,224,631 B1 | 5/2001 | Kohrs |
| 6,235,059 B1 * | 5/2001 | Benezech ............ A61F 2/4455 606/247 |
| 6,241,769 B1 | 6/2001 | Nicholson et al. |
| 6,241,771 B1 * | 6/2001 | Gresser ............... A61F 2/30965 606/77 |

(56) References Cited

U.S. PATENT DOCUMENTS

| | | | |
|---|---|---|---|
| 6,245,108 B1 * | 6/2001 | Biscup | A61F 2/4455 606/246 |
| 6,251,140 B1 | 6/2001 | Marino et al. | |
| 6,258,125 B1 | 7/2001 | Paul et al. | |
| 6,259,945 B1 | 7/2001 | Epstein et al. | |
| 6,264,651 B1 | 7/2001 | Underwood et al. | |
| 6,266,558 B1 | 7/2001 | Gozani et al. | |
| 6,273,905 B1 | 8/2001 | Streeter | |
| 6,277,149 B1 * | 8/2001 | Boyle | A61F 2/4465 623/16.11 |
| 6,292,701 B1 | 9/2001 | Prass et al. | |
| 6,306,100 B1 | 10/2001 | Prass | |
| 6,308,712 B1 | 10/2001 | Shaw | |
| 6,312,392 B1 | 11/2001 | Herzon | |
| 6,319,257 B1 | 11/2001 | Carignan et al. | |
| 6,325,764 B1 | 12/2001 | Griffith et al. | |
| 6,334,068 B1 | 12/2001 | Hacker | |
| 6,348,058 B1 | 2/2002 | Melkent et al. | |
| 6,360,750 B1 | 3/2002 | Gerber et al. | |
| 6,371,968 B1 | 4/2002 | Kogasaka et al. | |
| 6,371,989 B1 | 4/2002 | Chauvin et al. | |
| 6,383,221 B1 | 5/2002 | Scarborough et al. | |
| 6,409,766 B1 | 6/2002 | Brett | |
| 6,425,772 B1 | 7/2002 | Bernier et al. | |
| 6,425,859 B1 | 7/2002 | Foley et al. | |
| 6,425,901 B1 | 7/2002 | Zhu et al. | |
| 6,432,140 B1 | 8/2002 | Lin | |
| 6,440,142 B1 | 8/2002 | Ralph et al. | |
| 6,442,814 B1 | 9/2002 | Landry et al. | |
| 6,447,547 B1 | 9/2002 | Michelson | |
| 6,450,952 B1 | 9/2002 | Rioux et al. | |
| 6,451,015 B1 | 9/2002 | Rittman, III et al. | |
| 6,454,806 B1 | 9/2002 | Cohen et al. | |
| 6,466,817 B1 | 10/2002 | Kaula et al. | |
| 6,468,205 B1 | 10/2002 | Mollenauer et al. | |
| 6,468,207 B1 | 10/2002 | Fowler, Jr. | |
| 6,468,311 B2 | 10/2002 | Boyd et al. | |
| 6,491,724 B1 * | 12/2002 | Ferree | A61F 2/30742 623/17.11 |
| 6,500,128 B2 | 12/2002 | Marino | |
| 6,520,907 B1 | 2/2003 | Foley et al. | |
| 6,524,320 B2 | 2/2003 | DiPoto | |
| 6,527,773 B1 | 3/2003 | Lin et al. | |
| 6,535,759 B1 | 3/2003 | Epstein et al. | |
| D472,634 S | 4/2003 | Anderson | |
| D473,650 S | 4/2003 | Anderson | |
| 6,547,823 B2 | 4/2003 | Scarborough et al. | |
| 6,558,423 B1 | 5/2003 | Michelson | |
| 6,564,078 B1 | 5/2003 | Marino et al. | |
| 6,576,017 B2 | 6/2003 | Foley et al. | |
| 6,579,244 B2 | 6/2003 | Goodwin | |
| 6,595,998 B2 | 7/2003 | Johnson et al. | |
| 6,620,157 B1 | 9/2003 | Dabney et al. | |
| 6,626,905 B1 | 9/2003 | Schmiel et al. | |
| 6,635,086 B2 | 10/2003 | Lin | |
| 6,645,194 B2 | 11/2003 | Briscoe et al. | |
| 6,648,895 B2 | 11/2003 | Burkus et al. | |
| 6,672,019 B1 | 1/2004 | Wenz | |
| 6,676,703 B2 | 1/2004 | Biscup | |
| 6,679,833 B2 | 1/2004 | Smith et al. | |
| 6,706,067 B2 | 3/2004 | Shimp et al. | |
| 6,719,692 B2 | 4/2004 | Kleffner et al. | |
| 6,743,255 B2 | 6/2004 | Ferree | |
| 6,746,484 B1 * | 6/2004 | Liu | A61B 17/025 623/17.11 |
| 6,755,841 B2 | 6/2004 | Fraser et al. | |
| 6,760,616 B2 | 7/2004 | Hoey et al. | |
| 6,761,739 B2 | 7/2004 | Shepard | |
| 6,770,074 B2 | 8/2004 | Michelson | |
| 6,796,985 B2 | 9/2004 | Bolger et al. | |
| 6,810,281 B2 | 10/2004 | Brock et al. | |
| 6,819,956 B2 | 11/2004 | DiLorenzo | |
| 6,824,564 B2 | 11/2004 | Crozet | |
| 6,847,849 B2 | 1/2005 | Mamo et al. | |
| 6,849,047 B2 | 2/2005 | Goodwin | |
| 6,855,105 B2 | 2/2005 | Jackson, III et al. | |
| 6,871,099 B1 | 3/2005 | Whitehurst et al. | |
| D503,801 S | 4/2005 | Jackson | |
| 6,902,569 B2 | 6/2005 | Parmer et al. | |
| 6,923,811 B1 | 8/2005 | Carl et al. | |
| 6,923,814 B1 | 8/2005 | Hildebrand et al. | |
| 6,926,728 B2 | 8/2005 | Zucherman et al. | |
| 6,929,606 B2 | 8/2005 | Ritland | |
| 6,942,697 B2 * | 9/2005 | Lange | A61F 2/447 623/17.11 |
| 6,942,698 B1 | 9/2005 | Jackson | |
| 6,945,933 B2 | 9/2005 | Branch | |
| 6,951,538 B2 | 10/2005 | Ritland | |
| 6,964,687 B1 | 11/2005 | Bernard et al. | |
| 6,979,353 B2 | 12/2005 | Bresina | |
| 6,984,245 B2 | 1/2006 | McGahan et al. | |
| 6,986,788 B2 | 1/2006 | Paul et al. | |
| 6,989,031 B2 | 1/2006 | Michelson | |
| 7,018,416 B2 | 3/2006 | Hanson et al. | |
| 7,033,394 B2 | 4/2006 | Michelson | |
| 7,047,082 B1 | 5/2006 | Schrom et al. | |
| 7,050,848 B2 | 5/2006 | Hoey et al. | |
| 7,079,883 B2 | 7/2006 | Marino et al. | |
| 7,089,059 B1 | 8/2006 | Pless | |
| D530,423 S | 10/2006 | Miles et al. | |
| 7,177,677 B2 | 2/2007 | Kaula et al. | |
| 7,198,598 B2 | 4/2007 | Smith et al. | |
| 7,207,949 B2 | 4/2007 | Miles et al. | |
| 7,226,451 B2 | 6/2007 | Shluzas et al. | |
| 7,226,480 B2 * | 6/2007 | Thalgott | A61F 2/4455 623/17.11 |
| 7,261,688 B2 | 8/2007 | Smith et al. | |
| 7,470,236 B1 | 12/2008 | Kelleher et al. | |
| 7,473,222 B2 | 1/2009 | Dewey et al. | |
| 7,481,766 B2 | 1/2009 | Lee et al. | |
| 7,491,237 B2 * | 2/2009 | Randall | A61F 2/44 623/17.11 |
| 7,522,953 B2 | 4/2009 | Kaula et al. | |
| 7,556,601 B2 | 7/2009 | Branch et al. | |
| 7,582,058 B1 | 9/2009 | Miles et al. | |
| 7,643,884 B2 | 1/2010 | Pond et al. | |
| 7,691,057 B2 | 4/2010 | Miles et al. | |
| 7,717,959 B2 | 5/2010 | William et al. | |
| D620,110 S * | 7/2010 | Courtney | D24/155 |
| 7,763,078 B2 * | 7/2010 | Peterman | A61F 2/447 606/246 |
| 7,815,682 B1 * | 10/2010 | Peterson | A61F 2/4465 623/17.16 |
| 7,819,801 B2 | 10/2010 | Miles et al. | |
| 7,935,051 B2 | 5/2011 | Miles et al. | |
| 8,043,377 B2 * | 10/2011 | Guyer | A61F 2/30771 623/17.11 |
| 8,083,799 B2 * | 12/2011 | Baynham | A61F 2/447 606/246 |
| D653,756 S * | 2/2012 | Courtney | D24/155 |
| 8,216,312 B2 * | 7/2012 | Gray | A61B 17/7059 606/249 |
| 8,287,597 B1 * | 10/2012 | Pimenta | A61F 2/4611 623/17.16 |
| 8,328,856 B1 * | 12/2012 | Donahoe | 606/290 |
| 8,623,088 B1 * | 1/2014 | Tohmeh | A61F 2/4455 623/17.11 |
| 2001/0039949 A1 | 11/2001 | Loubser | |
| 2001/0056280 A1 | 12/2001 | Underwood et al. | |
| 2002/0007129 A1 | 1/2002 | Marino | |
| 2002/0010392 A1 | 1/2002 | Desai | |
| 2002/0058950 A1 | 5/2002 | Winterbottom et al. | |
| 2002/0072686 A1 | 6/2002 | Hoey et al. | |
| 2002/0077632 A1 | 6/2002 | Tsou | |
| 2002/0123780 A1 | 9/2002 | Grill et al. | |
| 2002/0138147 A1 * | 9/2002 | Cohen | A61F 2/4455 623/17.16 |
| 2002/0161415 A1 | 10/2002 | Cohen et al. | |
| 2002/0193843 A1 | 12/2002 | Hill et al. | |
| 2003/0032966 A1 | 2/2003 | Foley et al. | |
| 2003/0100950 A1 * | 5/2003 | Moret | A61F 2/4465 623/17.16 |
| 2003/0105503 A1 | 6/2003 | Marino | |

(56) References Cited

U.S. PATENT DOCUMENTS

| | | | |
|---|---|---|---|
| 2003/0105528 A1* | 6/2003 | Shimp | A61F 2/28 623/17.16 |
| 2003/0109928 A1* | 6/2003 | Pasquet | A61F 2/4611 623/17.11 |
| 2003/0125739 A1* | 7/2003 | Bagga | A61F 2/4455 606/247 |
| 2003/0139648 A1 | 7/2003 | Foley et al. | |
| 2003/0139812 A1* | 7/2003 | Garcia | A61B 17/1671 623/17.11 |
| 2003/0149341 A1 | 8/2003 | Clifton | |
| 2003/0153975 A1* | 8/2003 | Byrd, III | A61F 2/447 623/17.11 |
| 2003/0181981 A1* | 9/2003 | Lemaire | A61F 2/442 623/17.11 |
| 2003/0225405 A1 | 12/2003 | Weiner | |
| 2003/0236544 A1 | 12/2003 | Lunsford et al. | |
| 2004/0082999 A1* | 4/2004 | Mathys, Jr. | A61F 2/4455 623/17.11 |
| 2004/0117018 A1* | 6/2004 | Michelson | A61F 2/4455 623/17.11 |
| 2004/0127990 A1* | 7/2004 | Bartish, Jr. | A61F 2/4611 623/17.11 |
| 2004/0153155 A1 | 8/2004 | Chung et al. | |
| 2004/0158324 A1* | 8/2004 | Lange | A61L 31/126 623/17.11 |
| 2004/0199084 A1 | 10/2004 | Kelleher et al. | |
| 2004/0225228 A1 | 11/2004 | Ferree | |
| 2005/0004593 A1 | 1/2005 | Simonson | |
| 2005/0004623 A1 | 1/2005 | Miles et al. | |
| 2005/0010292 A1* | 1/2005 | Carrasco | A61F 2/4455 623/17.11 |
| 2005/0033380 A1 | 2/2005 | Tanner et al. | |
| 2005/0075578 A1 | 4/2005 | Gharib et al. | |
| 2005/0080320 A1 | 4/2005 | Lee et al. | |
| 2005/0119753 A1* | 6/2005 | McGahan | A61F 2/4465 623/17.16 |
| 2005/0143822 A1* | 6/2005 | Paul | A61F 2/4455 623/17.16 |
| 2005/0149035 A1 | 7/2005 | Pimenta et al. | |
| 2005/0177245 A1* | 8/2005 | Leatherbury | A61B 17/7059 623/23.5 |
| 2005/0182454 A1 | 8/2005 | Gharib et al. | |
| 2005/0187629 A1* | 8/2005 | Michelson | A61F 2/4455 623/17.11 |
| 2005/0192575 A1 | 9/2005 | Pacheco | |
| 2005/0197702 A1 | 9/2005 | Coppes et al. | |
| 2005/0216083 A1* | 9/2005 | Michelson | A61F 2/446 623/17.11 |
| 2006/0025703 A1 | 2/2006 | Miles et al. | |
| 2006/0041258 A1* | 2/2006 | Galea | A61F 2/4455 16/221 |
| 2006/0052828 A1 | 3/2006 | Kim et al. | |
| 2006/0069315 A1 | 3/2006 | Miles et al. | |
| 2006/0116766 A1* | 6/2006 | Lemaire | A61F 2/447 623/17.11 |
| 2006/0129244 A1* | 6/2006 | Ensign | A61F 2/4455 623/17.16 |
| 2006/0224078 A1 | 10/2006 | Hoey et al. | |
| 2006/0235520 A1* | 10/2006 | Pannu | A61B 17/025 623/17.11 |
| 2007/0016097 A1 | 1/2007 | Farquhar et al. | |
| 2007/0191945 A1 | 8/2007 | Yu et al. | |
| 2007/0198062 A1 | 8/2007 | Miles et al. | |
| 2007/0213826 A1* | 9/2007 | Smith | A61F 2/4465 623/17.11 |
| 2007/0233253 A1* | 10/2007 | Bray | A61F 2/4455 623/17.11 |
| 2007/0270972 A1 | 11/2007 | Gordon et al. | |
| 2007/0293782 A1 | 12/2007 | Marino | |
| 2008/0058606 A1 | 3/2008 | Miles et al. | |
| 2008/0064976 A1 | 3/2008 | Kelleher et al. | |
| 2008/0064977 A1 | 3/2008 | Kelleher et al. | |
| 2008/0065178 A1 | 3/2008 | Kelleher et al. | |
| 2008/0065219 A1* | 3/2008 | Dye | A61F 2/4465 623/17.16 |
| 2008/0071191 A1 | 3/2008 | Kelleher et al. | |
| 2008/0077247 A1* | 3/2008 | Murillo | A61F 2/30771 623/17.16 |
| 2008/0097164 A1 | 4/2008 | Miles et al. | |
| 2008/0154375 A1* | 6/2008 | Serhan | A61F 2/441 623/17.16 |
| 2008/0294262 A1* | 11/2008 | Levieux | A61F 2/447 623/17.16 |
| 2008/0300465 A1 | 12/2008 | Feigenwinter et al. | |
| 2008/0312742 A1* | 12/2008 | Abernathie | A61F 2/447 623/17.16 |
| 2009/0054987 A1* | 2/2009 | Chin | A61F 2/447 623/17.16 |
| 2009/0062917 A1* | 3/2009 | Foley | A61F 2/44 623/17.16 |
| 2009/0124860 A1 | 5/2009 | Miles et al. | |
| 2009/0138050 A1 | 5/2009 | Ferree | |
| 2009/0182430 A1* | 7/2009 | Tyber | A61F 2/4465 623/17.16 |
| 2009/0192403 A1 | 7/2009 | Gharib et al. | |
| 2009/0192613 A1* | 7/2009 | Wing | A61F 2/4465 623/17.11 |
| 2009/0198339 A1* | 8/2009 | Kleiner | A61F 2/446 623/17.16 |
| 2009/0204016 A1 | 8/2009 | Gharib et al. | |
| 2009/0210062 A1* | 8/2009 | Thalgott | A61F 2/4465 623/17.16 |
| 2009/0254182 A1* | 10/2009 | Kovarik | A61F 2/4611 623/17.11 |
| 2009/0299479 A1* | 12/2009 | Jones | A61F 2/4465 623/17.16 |
| 2010/0069783 A1 | 3/2010 | Miles et al. | |
| 2010/0130827 A1 | 5/2010 | Pimenta et al. | |
| 2010/0152603 A1 | 6/2010 | Miles et al. | |
| 2010/0152853 A1* | 6/2010 | Kirschman | A61F 2/447 623/17.11 |
| 2010/0160738 A1 | 6/2010 | Miles et al. | |
| 2010/0161057 A1* | 6/2010 | Berry | A61F 2/447 623/17.16 |
| 2010/0174148 A1 | 7/2010 | Miles et al. | |
| 2010/0228296 A1* | 9/2010 | Vraney | A61F 2/447 606/279 |
| 2010/0262246 A1* | 10/2010 | Attia | A61F 2/4465 623/17.16 |
| 2011/0040382 A1* | 2/2011 | Muhanna | A61F 2/4455 623/17.11 |
| 2011/0046736 A1* | 2/2011 | Graf | A61F 2/442 623/17.11 |
| 2011/0166657 A1* | 7/2011 | Thalgott | A61B 17/86 623/17.16 |
| 2011/0196493 A1* | 8/2011 | Pimenta | A61F 2/447 623/17.16 |
| 2011/0230970 A1* | 9/2011 | Lynn | A61F 2/442 623/17.16 |
| 2011/0245923 A1* | 10/2011 | Cobb | A61F 2/442 623/17.16 |
| 2011/0301710 A1* | 12/2011 | Mather | A61F 2/4611 623/17.16 |
| 2011/0313528 A1* | 12/2011 | Laubert | A61F 2/4455 623/17.16 |
| 2011/0319943 A1* | 12/2011 | Donahoe | A61B 17/7059 606/290 |
| 2011/0320000 A1* | 12/2011 | O'Neil | A61B 17/1671 623/17.16 |
| 2012/0078370 A1* | 3/2012 | James | A61F 2/442 623/17.16 |
| 2012/0089228 A1* | 4/2012 | Poulos | A61F 2/442 623/17.16 |
| 2012/0232664 A1* | 9/2012 | Ulrich, Jr. | A61F 2/4611 623/17.16 |
| 2012/0245690 A1* | 9/2012 | Cowan, Jr. | A61F 2/4465 623/17.16 |
| 2012/0277866 A1* | 11/2012 | Kalluri | A61F 2/442 623/17.16 |

(56) References Cited

U.S. PATENT DOCUMENTS

| | | | |
|---|---|---|---|
| 2012/0277867 A1* | 11/2012 | Kana | A61F 2/4455 623/17.16 |
| 2012/0303128 A1* | 11/2012 | Ullrich, Jr. | A61F 2/442 623/17.16 |
| 2012/0310351 A1* | 12/2012 | Farley | A61F 2/442 623/17.16 |
| 2012/0316649 A1* | 12/2012 | Johnston | A61F 2/447 623/17.16 |
| 2013/0018466 A1* | 1/2013 | Yu | A61F 2/4455 623/17.16 |
| 2013/0018471 A1* | 1/2013 | Davenport | A61L 27/042 623/17.16 |
| 2013/0023992 A1* | 1/2013 | Moskowitz | A61F 2/447 623/17.16 |
| 2013/0053967 A1* | 2/2013 | Sournac | A61B 17/8047 623/17.16 |
| 2013/0060336 A1* | 3/2013 | Hooper | A61F 2/447 623/17.11 |
| 2013/0060339 A1* | 3/2013 | Duffield | A61B 17/7059 623/17.16 |
| 2013/0066428 A1* | 3/2013 | Biedermann | A61B 17/8033 623/17.16 |
| 2013/0073044 A1* | 3/2013 | Gamache | A61F 2/442 623/17.16 |
| 2013/0073047 A1* | 3/2013 | Laskowitz | A61F 2/4455 623/17.16 |
| 2013/0096683 A1* | 4/2013 | Kube, II | A61F 2/442 623/17.16 |
| 2013/0116790 A1* | 5/2013 | Seifert | A61F 2/447 623/17.16 |
| 2013/0123923 A1* | 5/2013 | Pavlov | A61F 2/4455 623/17.16 |
| 2013/0131812 A1* | 5/2013 | Ganey | A61F 2/28 623/17.16 |
| 2013/0138214 A1* | 5/2013 | Greenhalgh | A61F 2/4455 623/17.16 |
| 2013/0158663 A1* | 6/2013 | Miller | A61F 2/4425 623/17.16 |
| 2013/0158664 A1* | 6/2013 | Palmatier | A61F 2/447 623/17.16 |
| 2013/0158669 A1* | 6/2013 | Sungarian | A61F 2/442 623/17.16 |
| 2013/0166027 A1* | 6/2013 | Bellas | A61F 2/447 623/17.16 |
| 2013/0190875 A1* | 7/2013 | Shulock | A61F 2/441 623/17.12 |
| 2013/0197642 A1* | 8/2013 | Ernst | A61F 2/4465 623/17.16 |
| 2013/0238095 A1* | 9/2013 | Pavento | A61B 17/7059 623/17.16 |
| 2013/0268080 A1* | 10/2013 | Melkent | A61F 2/4455 623/17.16 |
| 2013/0274883 A1* | 10/2013 | McLuen | A61F 2/447 623/17.16 |
| 2013/0297029 A1* | 11/2013 | Kana | A61F 2/447 623/17.16 |
| 2014/0012380 A1* | 1/2014 | Laurence | A61F 2/4465 623/17.16 |
| 2014/0025168 A1* | 1/2014 | Klimek | A61F 2/442 623/17.16 |
| 2014/0121777 A1* | 5/2014 | Rosen | A61F 2/4455 623/17.16 |
| 2014/0128977 A1* | 5/2014 | Glerum | A61F 2/4455 623/17.16 |
| 2014/0277495 A1* | 9/2014 | Muhanna | A61F 2/4455 623/17.16 |
| 2014/0379085 A1* | 12/2014 | Duffield | A61F 2/4455 623/17.16 |
| 2015/0018954 A1* | 1/2015 | Loebl | A61F 2/4425 623/17.16 |
| 2015/0045892 A1* | 2/2015 | Lynn | A61F 2/447 623/17.16 |
| 2015/0088256 A1* | 3/2015 | Ballard | A61B 17/708 623/17.11 |
| 2015/0100124 A1* | 4/2015 | Whipple | A61F 2/4455 623/17.15 |

FOREIGN PATENT DOCUMENTS

| | | |
|---|---|---|
| EP | 369603 | 5/1990 |
| EP | 517030 | 5/1992 |
| EP | 667127 | 8/1995 |
| EP | 706876 | 4/1996 |
| EP | 716840 | 6/1996 |
| EP | 737448 | 10/1996 |
| EP | 796593 | 9/1997 |
| EP | 880938 | 2/1998 |
| EP | 809974 | 4/1998 |
| EP | 809975 | 4/1998 |
| EP | 811356 | 4/1998 |
| EP | 0 972 538 | 1/2000 |
| FR | 2 795 624 | 1/2001 |
| WO | 90/00037 | 1/1990 |
| WO | 91/06261 | 5/1991 |
| WO | 92/14423 | 9/1992 |
| WO | 94/04100 | 3/1994 |
| WO | 94/10928 | 5/1994 |
| WO | 95/01810 | 1/1995 |
| WO | 96/08205 | 3/1996 |
| WO | 96/17564 | 3/1996 |
| WO | 96/41582 | 12/1996 |
| WO | 97/20513 | 6/1997 |
| WO | 97/33525 | 9/1997 |
| WO | 97/37620 | 10/1997 |
| WO | 98/09586 | 3/1998 |
| WO | 98/14142 | 4/1998 |
| WO | 98/17208 | 4/1998 |
| WO | 98/25539 | 6/1998 |
| WO | 99/08627 | 2/1999 |
| WO | 99/38461 | 8/1999 |
| WO | 00/38574 | 7/2000 |
| WO | 00/45712 | 8/2000 |
| WO | 00/45713 | 8/2000 |
| WO | 00/66217 | 11/2000 |
| WO | 00/67645 | 11/2000 |
| WO | 01/37728 | 5/2001 |
| WO | 01/41681 | 6/2001 |
| WO | 01/49333 | 7/2001 |
| WO | 02/054960 | 7/2002 |
| WO | 03/005887 | 1/2003 |
| WO | 03/026482 | 4/2003 |
| WO | 03/037170 | 5/2003 |
| WO | 2005/013805 | 2/2005 |
| WO | 2005/030318 | 4/2005 |
| WO | 2006/042241 | 4/2006 |
| WO | 2006/066217 | 6/2006 |

OTHER PUBLICATIONS

Dirksmeier et al., "Microendoscopic and Open Laminotomy and Discectomy in Lumbar Disc Disease" *Seminars in Spine Surgery*, 1999, 11(2): 138-146.

METRx Delivered Order Form, 1999, 13 pages.

Medtronic Sofamor Danek "METRx™ MicroDisectomy System," *Medtronic Sofamor Danek USA*, 2000, 21 pgs.

Medtronic Sofamor Danek "METRx System Surgical Technique," 2004, 22 pages.

"MetRx System MicroEndoscopic Discectomy: An Evolution in Minimally Invasive Spine Surgery," *Sofamor Danek*, 1999, 6 pages.

Smith and Foley "MetRx System MicroEndoscopic Discectomy: Surgical Technique" *Medtronic Sofamor Danek*, 2000, 24 pages.

"Sofamor Danek MED Microendoscopic Discectomy System Brochure" including Rapp "New endoscopic lumbar technique improves access preserves tissue" Reprinted with permission from: *Orthopedics Today*, 1998, 18(1): 2 pages.

Japanese Patent Office JP Patent Application No. 2006-528306 Office Action with English Translation, Jun. 10, 2009, 4 pages.

(56) References Cited

OTHER PUBLICATIONS

Axon 501(k) Notification: Epoch 2000 Neurological Workstation, Dec. 3, 1997, 464 pages.
Foley and Smith, "Microendoscopic Discectomy," *Techniques in Neurosurgery*, 1997, 3(4):301-307.
Medtronic Sofamor Danek "UNION™ / UNION-L™ Anterior & Lateral Impacted Fusion Devices: Clear choice of stabilization," *Medtronic Sofamor Danek*, 2000, 4 pages.
NuVasive Vector™ Cannulae, 2000, 1 page.
NuVasive Triad™ Tri-Columnar Spinal EndoArthrodesis™ via Minimally Invasive Guidance, 2000, 1 page (prior to Sep. 25, 2003).
NuVasive Triad™ Cortical Bone Allograft, 2000, 1 page (prior to Sep. 25, 2003).
NuVasive Vertebral Body Access System, 2000, 1 page.
Marina, "New Technology for Guided Navigation with Real Time Nerve Surveillance for Minimally Invasive Spine Discectomy & Arthrodesis," *Spineline*, 2000, p. 39.
NuVasive "INS-1 Screw Test," 2001, 10 pages.
NuVasive letter re 510k Neuro Vision JJB System, Oct. 16, 2001, 5 pages.
NuVasive letter re 510k Guided Arthroscopy System, Oct. 5, 1999, 6 pages.
NuVasive letter re 510k INS-1 Intraoperative Nerve Surveillance System, Nov. 13, 2000, 7 pages.
"NuVasiveTM Receives Clearance to Market Two Key Elem Minimally Invasive Spine Surgery System," Nov. 27, 2001, 20 pages.
Schick et al., "Microendoscopic lumbar discectomy versus open surgery: an intraoperative EMG study," *Eur Spine J*, 2002, 11: 20-26.
NuVasive letter re: 510(k) for Neurovision JJB System (Summary), Sep. 25, 2001, 28 pages.
NuVasive letter re: Special 510(k) Premarket Notification: Neurovision JJB System (Device Description), Jul. 3, 2003, 18 pages.
NuVasive letter re: Special 510(k) Premarket Notification: Neurovision JJB System (Device Description), Mar. 1, 2004, 16 pages.
NuVasive letter re: Special 510(k) Premarket Notification: Neurovision JJB System (Device Description), May 26, 2005, 17 pages.
NuVasive letter re: 510(k) Premarket Notification: Neurovision JJB System (Device Description), Jun. 24, 2005, 16 pages.
NuVasive letter re: Special 510(k) Premarket Notification: Neurovision JJB System (Device Description), Sep. 14, 2006, 17 pages.
NuVasive 510(k) Premarket Notification: Neurovision JJB System (Device Description), Aug. 20, 2007, 8 pages.
NuVasive letter re: 510(k) Premarket Notification: Guided Spinal Arthroscopy System (Device Description), Feb. 1, 1999, 40 pages.
NuVasive 510(k) Premarket Notification: Spinal System (Summary), Apr. 12, 2004, 10 pages.
NuVasive 510(k) Summary NIM Monitor, Sep. 4, 1998, 4 pages.
NuVasive correspondence re 510(k) Premarket Notification INS-1 Intraoperative Nerve Surveillance System: Section IV Device Description, pp. 12-51 (prior to Sep. 25, 2003).
Isley et al., "Recent Advances in Intraoperative Neuromonitoring of Spinal Cord Function: Pedicle Screw Stimulation Techniques," *American Journal of Electroneurodagnostic Technology*, Jun. 1997, 37(2): 93-126.
Mathews et al., "Laparoscopic Discectomy with Anterior Lumbar Interbody Fusion," *Spine*, 1995, 20(16): 1797-1802.
Rose et al., "Persistently Electrified Pedicle Stimulation Instruments in Spinal Instrumentation: Techniques and Protocol Development," *Spine*, 1997, 22(3): 334-343.
"Electromyography System," International Search report from International Application No. PCT/US00/32329, Apr. 27, 2001, 9 pages.
"Nerve Proximity and Status Detection System and Method," International Search Report from International Application No. PCT/US01/18606, dated Oct. 18, 2001, 6 pages.
"Relative Nerve Movement and Status Detection System and Method," International Search Report from International Application No. PCT/US01/18579, dated Jan. 15, 2002, 6 pages.

"System and Method for Determining Nerve Proximity Direction and Pathology During Surgery," International Search Report from International Application No. PCT/US02/22247, dated Mar. 27, 2003, 4 pages.
"System and Methods for Determining Nerve Direction to a Surgical Instrument," International Search Report from International Application No. PCT/US03/02056, dated Aug. 12, 2003, 5 pages.
"Systems and Methods for Performing Percutaneous Pedicle Integrity Assessments," International Search Report from International Application No. PCT/US02/35047, dated Aug. 11, 2003, 5 pages.
"Systems and Methods for Performing Surgery Procedures and Assessments," International Search Report from International Application No. PCT/US02/30617, dated Jun. 5, 2003, 4 pages.
Lenke et al., "Triggered Electromyographic Threshold for Accuracy of Pedicle Screw Placement," *Spine*, 1995, 20(4): 1585-1591.
"Brackmann II EMG System," *Medical Electronics*, 1999, 4 pages.
"Neurovision SE Nerve Locator/Monitor", RLN Systems Inc. Operators Manual, 1999, 22 pages.
"The Brackmann II EMG Monitoring System," Medical Electronics Co. Operator's Manual Version 1.1, 1995, 50 pages.
"The Nicolet Viking IV," Nicolet Biomedical Products, 1999, 6 pages.
Anderson et al., "Pedicle screws with high electrical resistance: a potential source of error with stimulus-evoked EMG," *Spine*, Department of Orthopaedic Surgery University of Virginia, Jul. 15, 2002, 27(14): 1577-1581.
Bose et al., "Neurophysiologic Monitoring of Spinal Nerve Root Function During Instrumented Posterior Lumber Spine Surgery," *Spine*, 2002, 27(13):1444-1450.
Calancie et al., "Stimulus-Evoked EMG Monitoring During Transpedicular Lumbosacral Spine Instrumentation" *Spine*, 1994, 19(24): 2780-2786.
Clements et al., "Evoked and Spontaneous Electromyography to Evaluate Lumbosacral Pedicle Screw Placement," *Spine*, 1996, 21(5): 600-604.
Danesh-Clough et al. ,"The Use of Evoked EMG in Detecting Misplaced Thoracolumbar Pedicle Screws," *Spine*, Orthopaedic Department Dunedin Hospital, Jun. 15, 2001, 26(12): 1313-1316.
Darden et al., "A Comparison of Impedance and Electromyogram Measurements in Detecting the Presence of Pedicle Wall Breakthrough," *Spine*, Charlotte Spine Center North Carolina, Jan. 15, 1998, 23(2): 256-262.
Ebraheim et al., "Anatomic Relations Between the Lumbar Pedicle and the Adjacent Neural Structures," *Spine*, Department of Orthopaedic Surgery Medical College of Ohio, Oct. 15, 1997, 22(20): 2338-2341.
Ford et al. "Electrical Characteristics of Peripheral Nerve Stimulators Implications for Nerve Localization," *Regional Anesthesia*, 1984, 9: 73-77.
Glassman et al., "A Prospective Analysis of Intraoperative Electromyographic Monitoring of Pedicle Screw Placement With Computed Tomographic Scan Confirmation," *Spine*, 1995, 20(12): 1375-1379.
Greenblatt et al., "Needle Nerve Stimulator-Locator: Nerve Blocks with a New Instrument for Locating Nerves," *Anesthesia& Analgesia*, 1962, 41(5): 599-602.
Haig, "Point of view," *Spine*, 2002, 27(24): 2819.
Haig et al., "The Relation Among Spinal Geometry on MRI, Paraspinal Electromyographic Abnormalities, and Age in Persons Referred for Electrodiagnostic Testing of Low Back Symptoms," *Spine*, Department of Physical Medicine and Rehabilitation University of Michigan, Sep. 1, 2002, 27(17): 1918-1925.
Holland et al., "Higher Electrical Stimulus Intensities are Required to Activate Chronically Compressed Nerve Roots: Implications for Intraoperative Electromyographic Pedicle Screw Testing," *Spine*, Department of Neurology, Johns Hopkins University School of Medicine, Jan. 15, 1998, 23(2): 224-227.
Holland, "Intraoperative Electromyography During Thoracolumbar Spinal Surgery," *Spine*, 1998, 23(17): 1915-1922.
Journee et al., "System for Intra-Operative Monitoring of the Cortical Integrity of the Pedicle During Pedicle Screw Placement in Low-Back Surgery: Design and Clinical Results," *Sensory and Neuromuscular Diagnostic Instrumentation and Data Analysis I,*

(56) References Cited

OTHER PUBLICATIONS

*18th Annual International Conference on Engineering in Medicine and Biology Society*, Amsterdam, 1996, pp. 144-145.

Maguire et al., "Evaluation of Intrapedicular Screw Position Using Intraoperative Evoked Electromyography," *Spine*, 1995, 20(9): 1068-1074.

Martin et al. "Initiation of Erection and Semen Release by Rectal Probe Electrostimulation (RPE)," *The Journal of Urology*, The Williams& Wilkins Co., 1983, 129: 637-642.

Minahan et al., "The Effect of Neuromuscular Blockade on Pedicle Screw Stimulation Thresholds" *Spine*, Department of Neurology, Johns Hopkins University School of Medicine, Oct. 1, 2000, 25(19): 2526-2530.

Pither et al., "The Use of Peripheral Nerve Stimulators for Regional Anesthesia: Review of Experimental Characteristics Technique and Clinical Applications," *Regional Anesthesia*, 1985, 10:49-58.

Raj et al., "Infraclavicular Brachial Plexus Block—A New Approach" *Anesthesia and Analgesia*, 1973, (52)6: 897-904.

Raj et al., "The Use of Peripheral Nerve Stimulators for Regional Anesthesia," *Clinical Issues in Regional Anesthesia*, 1985, 1(4):1-6.

Raj et al., "Use of the Nerve Stimulator for Peripheral Blocks," *Regional Anesthesia*, Apr.-Jun. 1980, pp. 14-21.

Raymond et al., "The Nerve Seeker: A System for Automated Nerve Localization," *Regional Anesthesia*, 1992, 17(3): 151-162.

Shafik, "Cavernous Nerve Simulation through an Extrapelvic Subpubic Approach: Role in Penile Erection," *Eur. Urol*, 1994, 26: 98-102.

Toleikis et al., "The Usefulness of Electrical Stimulation for Assessing Pedicle Screw Replacements," *Journal of Spinal Disorder*, 2000, 13(4): 283-289.

Medtronic Sofamor Danek "UNION™ / UNION-L™ Anterior & Lateral Impacted Fusion Devices: Surgical Technique" *Medtronic Sofamor Danek*, 2001, 20 pages.

Bergey et al., "Endoscopic Lateral Transpsoas Approach to the Lumbar Spine," *Spine*, 2004, 29(15): 1681-1688.

Dezawa et al., "Retroperitoneal Laparoscopic Lateral Approach to the Lumbar Spine: A New Approach, Technique, and Clinical Trial," *Journal of Spinal Disorders*, 2000, 13(2): 138-143.

Gardocki, "Tubular diskectomy minimizes collateral damage: A logical progression moves spine surgery forward," *AAOS Now*, 2009, 5 pages.

Hovorka et al., "Five years' experience of retroperitoneal lumbar and thoracolumbar surgery," *Eur Spine J.*, 2000, 9(1): S30-S34.

Kossmann et al., "The use of a retractor system (SynFrame) for open, minimal invasive reconstruction of the anterior column of the thoracic and lumbar spine," *Eur Spine J.*, 2001, 10: 396-402.

Mayer, "A New Microsurgical Technique for Minimally Invasive Anterior Lumbar Interbody Fusion," *Spine*, 1997, 22(6): 691-699.

Mayer, "The ALIF Concept," *Eur Spine J.*, 2000, 9(1): S35-S43.

Mayer and Wiechert, "Microsurgical Anterior Approaches to the Lumbar Spine for Interbody Fusion and Total Disc Replacement," *Neurosurgery*, 2002, 51(2): 159-165.

McAfee et al., "Minimally Invasive Anterior Retroperitoneal Approach to the Lumbar Spine: Emphasis on the Lateral BAK," *Spine*, 1998, 23(13): 1476-1484.

Rao, et al. "Dynamic retraction of the psoas muscle to expose the lumbar spine using the retroperitoneal approach," *J. Neurosurg Spine*, 2006, 5: 468-470.

Wolfla et al., "Retroperitoneal lateral lumbar interbody fusion with titanium threaded fusion cages," *J. Neurosurg (Spine 1)*, 2002, 96: 50-55.

Larson and Maiman, "Surgery of the Lumbar Spine," Thieme Medical Publishers, Inc., 1999, pp. 305-319.

Medtronic XOMED Surgical Products, Inc., NIM-Response Nerve Integrity Monitor Intraoperative EMG Monitor User's Guide, Revision B, 2000, 47 pages.

"NuVasive's spine surgery system cleared in the US," Pharm & Medical Industry Week, Dec. 10, 2001, 1 page.

Pimenta, "Initial Clinical Results of Direct Lateral, Minimally Invasive Access to the Lumbar Spine for Disc Nucleus Replacement Using a Novel Neurophysiological Monitoring System." *The 9th IMAST*, May 2002, 1 page.

Pimenta et al., "The Lateral Endoscopic Transpsoas Retroperitoneal Approach (Letra) for Implants in the Lumbar Spine," *World Spine II—Second Interdisciplinary Congress on Spine Care*, Aug. 2003, 2 pages.

Crock, H.V. MD., "Anterior Lumbar Interbody Fusion," Clinical Orthopaedics and Related Research, Number One Hundred Sixty Five, 1982, pp. 157-163, 13 pages.

Mayer and Brock, "Percutaneous endoscopic discectomy: surgical technique and preliminary results compared to microsurgical discectomy," *J. Neurosurg*, 1993, 78: 216-225.

Schaffer and Kambin, "Percutaneous Posterolateral Lumbar Discectomy and Decompression with a 6.9-Millimeter Cannula," *The Journal of Bone and Joint Surgery*, 1991, 73A(6): 822-831.

Friedman, "Percutaneous discectomy: An alternative to chemonucleolysis," *Neurosurgery*, 1983, 13(5): 542-547.

Brau, "Chapter 22: Anterior Retroperitoneal Muscle-Sparing approach to L2-S1 of the Lumbar Spine," *Surgical Approaches to the Spine*. Robert G. Watkins, MD. (ed) 2003. pp. 165-181.

Kossmann et al., "Minimally Invasive Vertebral Replacement with Cages in Thoracic and Lumbar Spine," *European Journal of Trauma*, 2001, 27: 292-300.

Mayer H. M. (ed.) *Minimally Invasive Spine Surgery: A Surgical Manual*. 2000. 51 pages.

Pimenta et al., "Implante de protese de nucleo pulpost: analise inicial," *Journal Brasileiro de Neurocirurgia*, 2001, 12(2): 93-96.

Traynelis, "Spinal Arthroplasty," *Neurological Focus*, 2002, 13(2): 12 pages.

Zdeblick, Thomas A. (ed.). Anterior Approaches to the Spine. 1999. 43 pages.

CoRoent™ Marketing Brochure (9004001 A.0), *NuVasive, Inc.*, 2004, 2 pages.

CoRoent™ Marketing Brochure (9004001 C.0), *NuVasive, Inc.*, 2005, 2 pages.

CoRoent™ XL & XLR Marketing Brochure (9004225 A.0), *NuVasive, Inc.*, 2005, 2 pages.

CoRoent® XL & XLR Marketing Brochure (9004225 B.0), *NuVasive, Inc.*, 2006, 2 pages.

CoRoent® XL & XLR Marketing Brochure (9004225 C.0), *NuVasive, Inc.*, 2007, 2 pages.

CoRoent® XL Marketing Brochure (9500039 A.0), *NuVasive, Inc.*, 2006, 8 pages.

Baulot et al., "Complementary anterior spondylodesis by thoracoscopy. Technical note regarding an observation", *Lyon Surg.*, 90(5):347-351 (1994).

Berry et al., "A morphometric study of human lumbar and selected thoracic vertebrae, study of selected vertebrae" *Spine* 12(4):362-367 (1996).

Crock, H. V., "A Short Practice of Spinal Surgery", Second, revised edition, published by Springer-Verlag/Wein, New York (1993).

Edeland, H.G. "Some additional suggestions for an intervertebral disc prosthesis", *Journal of Biomedical Engineering*, 7:57-62 (1985).

Kemp, H. B. S., "Anterior fusion of the spine for infective lesions in adults", *Journal of Bone & Joint Surgery*, 55B(4):715-734 (1973).

Alleyne et al., "Current and future approaches to lumbar disc surgery: A literature review", *Medscape Orthopedics & Sports Medicine*, 1, [www.medscape.com/Medscape/OrthoSportsMed/1997/v01.n11/.../mos3057], (1997).

Benini et al., "Undercutting decompression and posterior fusion with translaminar facet screw fixation in degenerative lumbar spinal stenosis: Technique and results", *Neuro-Orthopedics*, 17/18, 159-172 (1995).

Kambin, et al., "History and current status of percutaneous arthroscopic disc surgery", *Spine*, 21(24S):57S-61S (1996).

Stein et al., "Percutaneous facet joint fusion: Preliminary experience", *Journal of Vascular and Interventional Radiology*, 4:69-74 (1993).

(56) References Cited

OTHER PUBLICATIONS

Vamvanu et al., "Surgical treatment of internal disc disruption: An outcome study of four fusion techniques", *Journal of Spinal Disorders*, 11(5):375-382 (1998).

Damasceno et al., Lumbar Lordosis: A Study of Angle Values and of Vertebral Bodies and Intervertebral Discs Role, *Acta Ortol Bras*, 12(4):193-198 (2006).

\* cited by examiner

METHODS AND APPARATUS FOR PERFORMING SPINE SURGERY

CROSS-REFERENCE TO RELATED APPLICATIONS

This application is a continuation of U.S. patent application Ser. No. 14/578,215 filed Dec. 19, 2014, pending, which is a continuation of U.S. patent application Ser. No. 13/653, 335 filed Oct. 16, 2012 (now U.S. Pat. No. 8,920,500), which is a continuation of U.S. patent application Ser. No. 12/799,021 filed Apr. 16, 2010 (now U.S. Pat. No. 8,287, 597), which claims the benefit of priority from U.S. Provisional Patent Application Ser. No. 61/212,921 filed Apr. 16, 2009, and U.S. Provisional Patent Application Ser. No. 61/319,823 filed Mar. 31, 2010, the entire contents of which is hereby expressly incorporated by reference into this disclosure as if set forth in its entirety herein.

FIELD

The present invention relates to implants and methods for adjusting sagittal imbalance of a spine.

BACKGROUND

A human spine has three main regions—the cervical, thoracic, and lumbar regions. In a normal spine, the cervical and lumbar regions have a lordotic (backward) curvature, while the thoracic region has a kyphotic (forward) curvature. Such a disposition of the curvatures gives a normal spine an S-shape. Sagittal imbalance is a condition in which the normal alignment of the spine is disrupted in the sagittal plane causing a deformation of the spinal curvature. One example of such a deformity is "flat-back" syndrome, wherein the lumbar region of the spine is generally linear rather than curved. A more extreme example has the lumbar region of the spine exhibiting a kyphotic curvature such that the spine has an overall C-shape, rather than an S-shape. Sagittal imbalance can be a problem in that it is biomechanically disadvantageous and generally results in discomfort, pain, and an awkward appearance in that the patient tends to be bent forward excessively.

Various treatments for sagittal imbalance are known in the art. These treatments generally involve removing at least some bone from a vertebra (osteotomy) and sometimes removal of the entire vertebra (vertebrectomy), in order to reduce the posterior height of the spine in the affected region and recreate lordotic curve. Such procedures are traditionally performed via an open, posterior approach involving a large incision (often to expose multiple spinal levels at the same time) and require stripping of the muscle tissue away from the bone. These procedures can have the disadvantages of a large amount of blood loss, high risk, and a long and painful recovery for the patient. Furthermore, depending upon the patient, multiple procedures, involving both anterior and posterior approaches to the spine, may be required.

The present invention is directed at overcoming, or at least improving upon, the disadvantages of the prior art.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF A PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The methods and devices described herein include a variety of inventive features and components that warrant patent protection, both individually and in combination.

Figure 1:
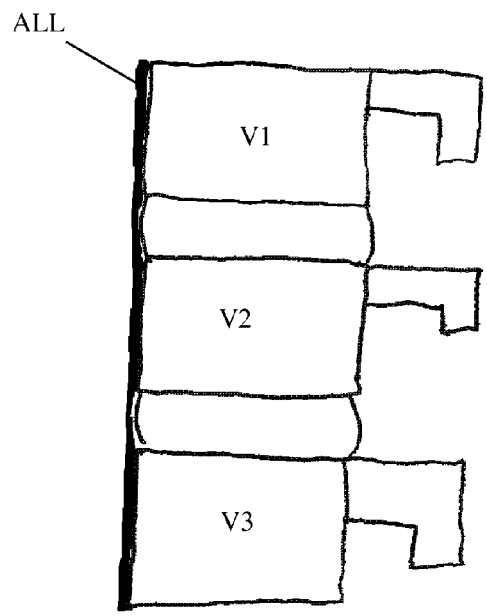
FIG. 1 is a lateral view representing a portion of a sagitally imbalanced lumbar spine lacking the normal lordotic curvature.
Figure 2:
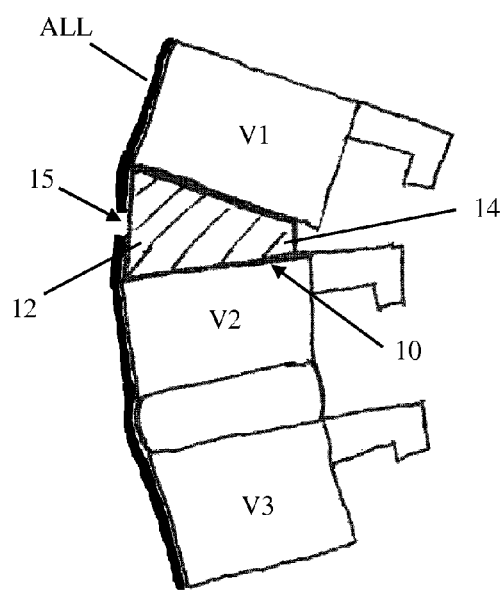
FIG. 2 is a side view representing the lumbar spine of FIG. 1 after restoration of the lordotic curvature using a hyper-lordotic fusion implant, according to one example embodiment.

With reference to FIGS. 1-2, devices and methods of the present invention are utilized to correct sagittal imbalance, including lumbar kyphosis, by increasing the anterior height of the affected spinal area (as opposed to reducing the posterior height). FIG. 1 illustrates a portion of the lumbar spine lacking the standard lordotic curvature. To correct the sagittal imbalance, illustrated in FIG. 2, a hyper-lordotic implant 10 is positioned into the disc space at the appropriate spinal level (e.g. between V1 and V2). An anterior sidewall 12 of hyper-lordotic implant 10 has a height significantly larger than an opposing posterior sidewall 14 such that when the implant is positioned within the disc space the anterior aspects of V1 and V2 are forced apart while the posterior aspects are not (or at least not to the same degree), thus imparting a lordotic curvature into the spine. To allow the anterior aspects of V1 and V2 to separate and receive the hyper-lordotic implant 10, the Anterior Longitudinal Ligament (ALL) that runs along the anterior aspect of the spine may be released or cut (15). According to a preferred method, the implant 10 is implanted through a lateral access corridor formed through the side of the patient. Accessing the targeted spinal site through the lateral access corridor avoids a number of disadvantages associated with posterior access (e.g. cutting through back musculature and possible need to reduce or cut away part of the posterior bony structures like lamina, facets, and spinous process) and anterior access (e.g. use of an access surgeon to move various organs and blood vessels out of the way in order to reach the target site). Accordingly, by accessing the target site via a lateral access approach and correcting the sagittal imbalance without reducing the posterior height (i.e. no bone removal) the high blood loss and painful recovery associated previous methods may be avoided (or at least mitigated).

Figure 3:
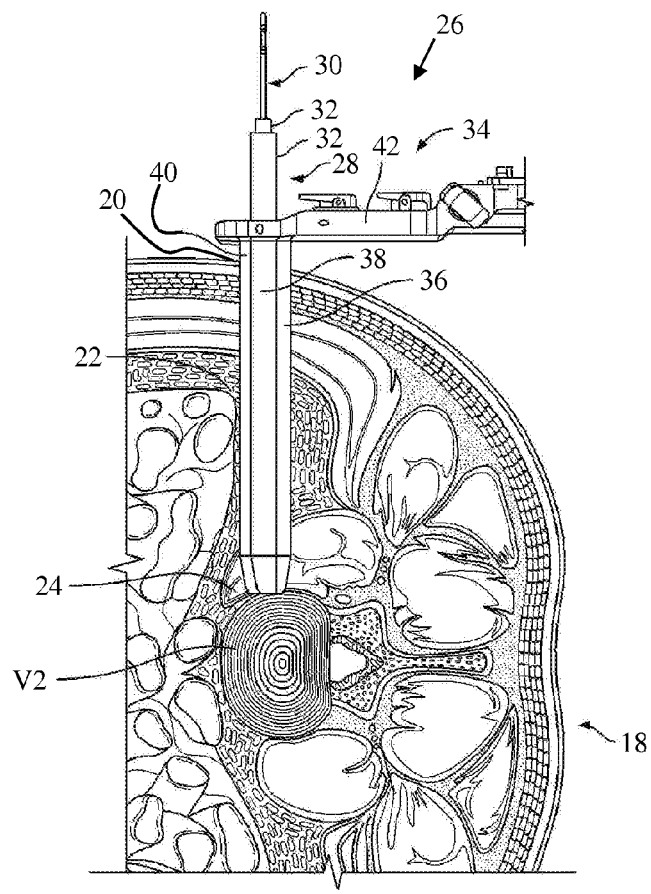
FIG. 3 is a top down view depicting the creation of a lateral access corridor formed with a surgical access system through the side of the patient to the target disc space, according to one example embodiment.
Figure 4:
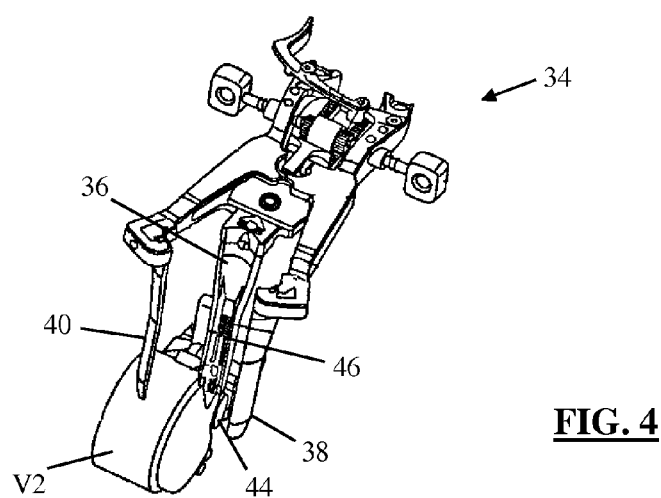
FIG. 4 is a perspective view depicting a lateral access corridor formed with a retractor assembly through the side of the patient to the target disc space, according to one example embodiment.
Figure 5:
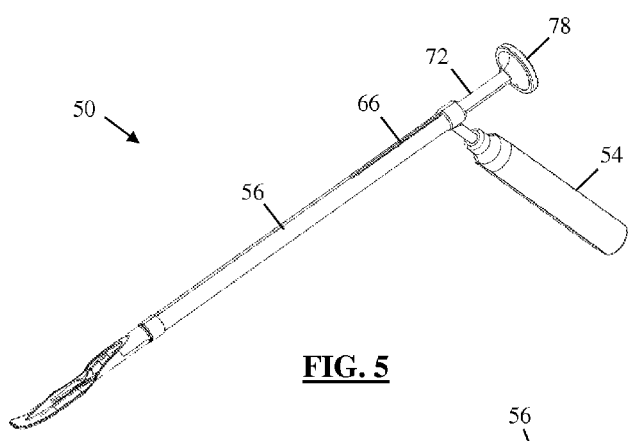
FIG. 5 is a front perspective view of an Anterior Longitudinal Ligament (ALL) resector for safely releasing the ALL through a lateral access corridor, according to one example embodiment.
Figure 6:
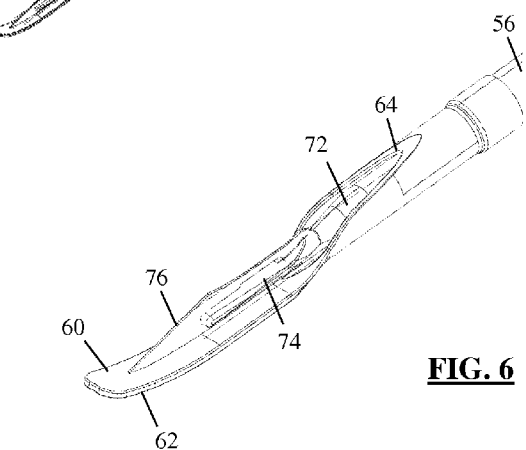
FIG. 6 is an enlarged from perspective view of the distal portion of the ALL resector of FIG. 5.
Figure 7:
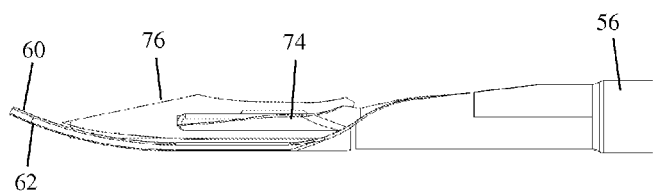
FIG. 7 is an enlarged side view of the distal portion of the ALL resector of FIG. 5.
Figure 8:
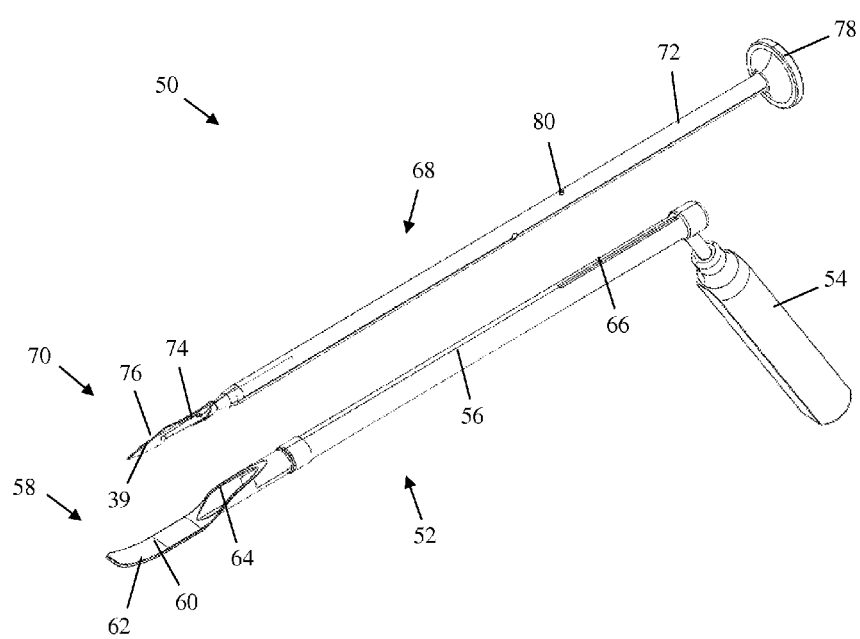
FIG. 8 is an exploded front perspective view of the ALL resector of FIG. 5.
Figure 9:
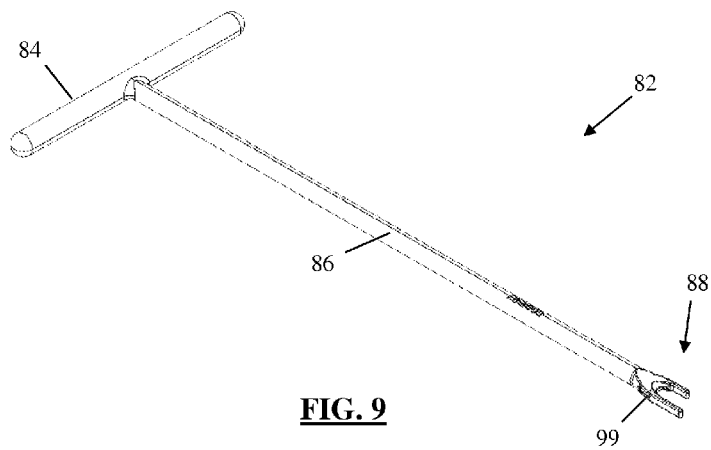
FIG. 9 is a front perspective view of an ALL resector for safely releasing the ALL through a lateral access corridor, according to another example embodiment.
Figure 10:
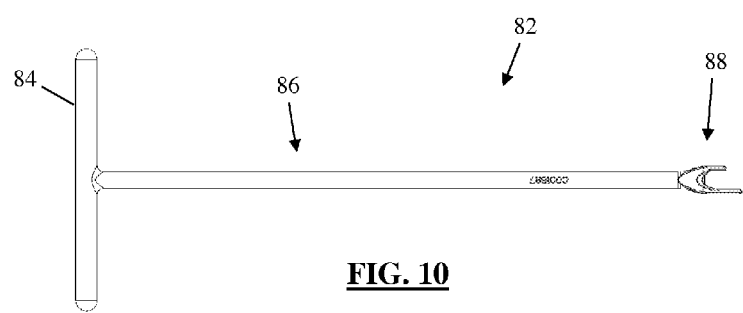
FIG. 10 is a side view of the ALL resector of FIG. 9.

According to one example, the lateral access approach to the targeted spinal space may be performed according to the instruments and methods described in commonly owned U.S. Pat. No. 7,207,949 entitled "Surgical Access System and Related Methods," and/or U.S. patent application Ser. No. 10/967,668 entitled "Surgical Access System and Related Methods," the entire contents of which are each incorporated herein by reference as if set forth herein in their entireties. With reference to FIGS. 3-4, a discussion of the lateral access instruments and methods is provided in brief detail. With the patient 20 positioned on their side, a surgical access system 20 is advanced through an incision 20, into the retroperitoneal space 22, and then through the psoas muscle 24 until the targeted spinal site (e.g. the disc space between V1 and V2) is reached. The access system 26 may include at least one tissue dilator, and preferably includes a sequential dilation system 28 with an initial dilator 30 and one or more additional dilators 32 of increasing diameter, and a tissue retractor assembly 34. As will be appreciated, the initial dilator 30 is preferably advanced to the target site first, and then each of the additional dilators 32 of increasing diameter are advanced in turn over the previous dilator. A k-wire (not shown) may be advanced to the target site and docked in place (for example, by inserting the k-wire into the vertebral disc) prior to, in concurrence with, or after advancing the initial dilator 30 to the target site. With the sequential dilation system 28 positioned adjacent the target site (and optionally docked in place via the k-wire), the retractor assembly 34 is then advanced to the target site over the sequential dilation system 28. According to the embodiment shown, the retractor assembly 34 includes retractor blades 36, 38, 40 and a body 42. With the sequential dilation system 28 removed, the retractor blades 36, 38, and 40 are separated (FIG. 4), providing the lateral access corridor through which instruments may be advanced to prepare the disc space and insert the implant 10. According to one example, the posterior blade 36 may be fixed in position relative to the spine prior to opening the retractor blades. This may be accomplished, for example by attaching a shim to the blade 36 (e.g. via track 44 including dove tail grooves formed on the interior of blade 36) and inserting the distal end of the shim into the disc space. In this manner, the posterior blade 36 will not move posteriorly (towards nerve tissue located in the posterior portion of the psoas muscle). Instead, the blades 38 and 40 will move away from the posterior blade 36 to expand the access corridor. Additionally, nerve monitoring (including determining nerve proximity and optionally directionality) is preferably performed as each component of the access system 26 is advanced through the psoas muscle, protecting the delicate nerve tissue running through the psoas, as described in the '949 patent and '668 application. Monitoring the proximity of nerves also allows the posterior blade 36 of the retractor assembly 34 to be positioned very posterior (all the way back to the exiting nerve roots), thus exposing a greater portion of the disc space than would otherwise be safely achievable. This inturn permits full removal of the disc and implantation of a wider implant and the wider implant makes utilization of the hyper-lordotic implant with a large lordotic angle (e.g. between 20-40 degrees) more practical.

With the lateral access corridor formed (as pictured in FIG. 4) the target site may be prepped for insertion of the implant 10. Preparation of the disc space may include performing an annulotomy, removal of disc material, and abrasion of the endplates and instruments such as annulotomy knives, pituitaries, curettes, disc cutters, endplate scrapers may be used. Additionally, as discussed above, it may generally be necessary to release the ALL in order to create enough flexibility between the adjacent vertebrae (e.g. V1 and V2) to receive the hyper-lordotic implant 10. Unlike an anterior approach (where the great vessels and other tissue lying anterior to the disc space is retracted during the approach), when the target disc is approached laterally, the great vessels remain adjacent to the ALL along the anterior face of the spine. Thus, while cutting the ALL is generally simple and necessary during an anterior approach surgery, cutting the ALL during a lateral approach surgery has typically been unnecessary and can be difficult because of the need to avoid damaging the great vessels. Accordingly, FIGS. 5-14 set forth various example embodiments of ALL resecting instruments for safely releasing the ALL from a lateral approach.

FIGS. 5-8 illustrate one example ALL resector 50. The ALL resector 50 includes a tissue retractor 52 and a sliding blade 68 and functions to both sever the ALL and protect surrounding tissue (e.g. great vessels, nerves etc. . . . ) from unwanted damage while the ALL is being severed. The tissue retractor 52 includes a handle 54, hollow shaft 56, and head 58. The head 58 is curved, preferably such that the inside surface 60 complements the curvature of the anterior aspects of the spinal target site. The head 58 may thus be positioned through the lateral access corridor to the spine and such that the curved interior surface 60 nestles around the anterior curved anterior aspect of the spine. The outside surface 62 will form a barrier, protecting tissue along the anterior spine from inadvertent contact with the sliding blade when the ALL is cut. Furthermore, the tissue retractor 52 can be further manipulated move tissue and further expose the anterior aspect of the target site. The hollow shaft 56 includes a central lumen 64 with an opening adjacent the head 58 and another opening at the opposing end such that the sliding blade 68 may travel through the shaft 56.

The sliding blade 68 includes a blade 70 that is secured to the distal end of an extender 72 by way of an attachment feature 74. The attachment feature 74 as shown is similar to known attachment features used for attaching a blade at the end of a scalpel. It will be appreciated that any number of mechanisms may be used to attach blade 70 to extender 72. Blade 70 may be disposable and extender 72 may be reusable. Alternatively, both blade 70 and extender 72 may be reusable or both may be disposable. The blade 70 includes a cutting edge 76 that, when advanced beyond the lumen 64 of shaft 56, cuts through tissue or material situated adjacent the cutting edge 76.

The proximal end of the extender 72 includes a grip 78 that a user may use to manipulate the position of the sliding blade 68 relative to the shaft 56 and head 58. At least one stop feature 80 extends from the outer surface of the extender 72 which engages with a track 66 that extends along a portion of the elongated shaft 56. The track 66 limits the longitudinal travel of the sliding blade 68 relative to the shaft 56 so that the sliding blade 68 remains slidably mated to the tissue retractor 52 without becoming unassembled and such that the blade 70 cannot extend beyond the protective head 58. Additionally, the stop feature 80 restricts rotation of the sliding blade 68 relative to the tissue retractor 52.

Figure 11:
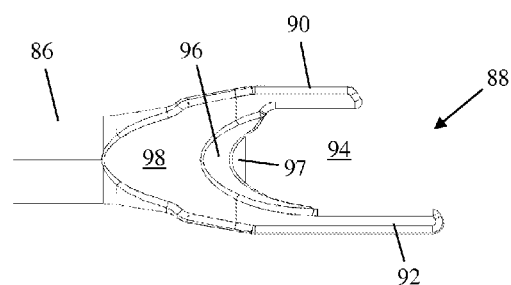
FIG. 11 is an enlarged side view of the distal end of the ALL resector of FIG. 9.
Figure 12:
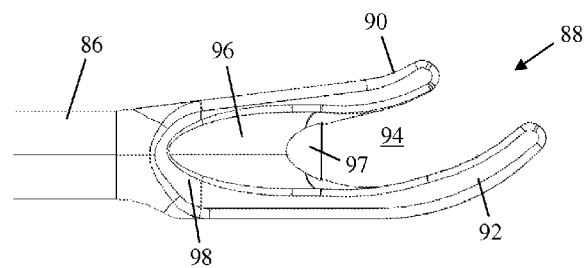
FIG. 12 is an enlarged side view of the distal end of the ALL resector of FIG. 9 having curved finger portions.

FIGS. 9-12 illustrate another example embodiment of an ALL resector 82. The ALL resector 82 includes a handle 84 (for example, a T-handle) located at the proximal end of the elongated shaft 86 and a distal head 88 for resecting the ALL. The distal head 88 includes distally extending first and second fingers 90, 92, which form an opening 94 therebetween. First and second tapered surfaces 96, 98 which extend a distance from the elongated shaft 86 along the fingers 90, 92 enable the distal head 88 to insert gently between tissue. As best shown in FIG. 11, the first finger 90 may be shorter in length than the second finger 92. However, the first and second finger 90, 92 may be provided in any number of length configurations without departing from the scope of the present invention. By way of example, it has been contemplated that the first finger 90 may be completely removed. Alternatively, as pictured in FIG. 12, the fingers 90 and 92 may be curved and have a more substantial width than shown in FIGS. 9-11. The curvature of the first and second fingers allows the distal head 88 to follow closely along the anterior side of the spine and/or along a curved spatula (not shown) positioned adjacent the anterior side of the vertebral body. Though not shown, a user may optionally insert a spatula along the anterior portion of the ALL prior to inserting the ALL resector 82. The spatula may serve as additional protection between the delicate tissue anterior to the ALL and the cutting blade 97 of the ALL resector 82. With a spatula in place the user may insert the distal head 88 such that it approaches the lateral side of the ALL and is guided along the inside edge of the spatula. By way of example, the spatula may be straight or curved to match the selected fingers of the distal head 88.

A cutting blade 97 is exposed between the first and second fingers 90, 92 in the opening 94. A slot 99 formed along a side of the distal head 88 allows a cutting blade 97 to be inserted and removed from the distal head 88. Thus, the cutting blade 97 may be disposable and the remainder of the ALL resector 82 may be reusable. Alternatively, both cutting blade 97 and remainder of the ALL resector 82 may be reusable or both may be disposable. In use, the ALL resector 82 is preferably positioned such that the second finger 92 is aligned along the anterior side of the ALL and the first finger 90 is aligned along the posterior side of the ALL, thus, at least partially bounding the ALL on either side. The ALL resector 82 is advanced forward so that the cutting blade 97 cuts through the ALL from one lateral edge to the other. As discussed above, the second finger 92 is preferably aligned along the anterior side of the ALL as the distal head 88 is advanced, thereby shielding the tissue lying anterior to the finger 92 (e.g. great vessels, etc. . . . ) from the cutting blade 97. Furthermore, as the user advances the ALL resector 82, the fingers 90, 92 may also act as a stabilizing guide.

Figure 13:
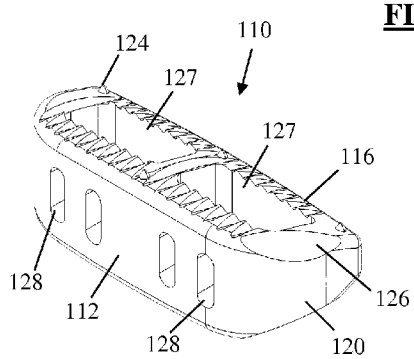
FIGS. 13-15 are anterior-front perspective, posterior-rear perspective, and front views of a hyper-lordotic lateral implant according to one example embodiment.
Figure 14:
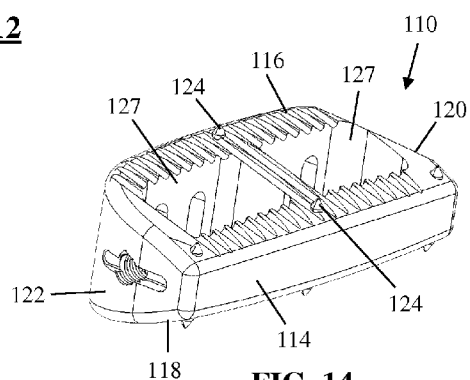
Figure 15:
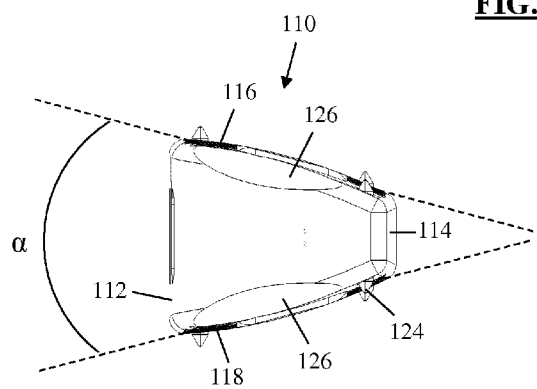

Turning now to FIGS. 13-19, various embodiments of the hyper-lordotic implant 10 are described. FIGS. 13-15, for example, illustrate an example implant 110. Implant 110 may preferably be comprised of any suitable non-bone composition having suitable radiolucent characteristics, including but not limited to polymer compositions (e.g. poly-ether-ether-ketone (PEEK) and/or poly-ether-ketone-ketone (PEKK)) or any combination of PEEK and PEKK. Other materials such as for example, metal, ceramics, and bone may also be utilized for the implant 110. Implant 110 has a top surface 116 and bottom surface 118 for contacting V1 and V2, anterior sidewall 112, posterior sidewall 114, and front or leading side 120, and rear or trailing side 122. As discussed, the anterior sidewall 112 has a height greater than the posterior sidewall 114 such that the top surface 116 and bottom surface 118 converge towards each other in the posterior direction. By way of example, the top and bottom surfaces may converge at an angle between 20 and 40 degrees. It is contemplated that variations of the implant 110 may be simultaneously provided such that the user may select from different available ranges. For example, variations may be provided with 20 degree, 30 degree, and 40 degree angles. The top and bottom surfaces may be planar or provided as convex to better match the natural contours of the vertebral end plates. The length of the implant 110 is such that it may span from one lateral aspect of the disc space to the other, engaging the apophyseal ring on each side. By way of example, the implant 110 may be provided with a length between 40 and 60 mm.

Having been deposited in the disc space, the implant 110 facilitates spinal fusion over time by maintaining the restored curvature as natural bone growth occurs through and/or past the implant 110, resulting in the formation of a boney bridge extending between the adjacent vertebral bodies.

The implant 110 may be provided with any number of additional features for promoting fusion, such as apertures 127 extending between the top and bottom surfaces 116, 118 which allow a boney bridge to form through the implant 110. Various osteoinductive materials may be deposited within the apertures 127 and/or adjacent to the implant 110 to further facilitate fusion. Such osteoinductive materials may be introduced before, during, or after the insertion of the exemplary spinal fusion implant 110, and may include (but are not necessarily limited to) autologous bone harvested from the patient receiving the spinal fusion implant, bone allograft, bone xenograft, any number of non-bone implants (e.g. ceramic, metallic, polymer), bone morphogenic protein, and bio-resorbable compositions, including but not limited to any of a variety of poly (D,L-lactide-co-glycolide) based polymers. Visualization apertures 128 situated along the sidewalls, may aid in visualization at the time of implantation and at subsequent clinical evaluations. More specifically, based on the generally radiolucent nature of the preferred embodiment of implant 110, the visualization apertures 128 provide the ability to visualize the interior of the implant 110 during X-ray and/or other suitable imaging techniques. Further, the visualization apertures 128 will provide an avenue for cellular migration to the exterior of the implant 110. Thus the implant 110 will serve as additional scaffolding for bone fusion on the exterior of the implant 110.

The implant 110 also preferably includes anti-migration features designed to increase the friction between the implant 110 and the adjacent contacting surfaces of the vertebral bodies V1 and V2 so as to prohibit migration of the implant 110 after implantation. Such anti-migration features may include ridges provided along the top surface 116 and/or bottom surface 118. Additional anti-migration features may also include spike elements 124 disposed along the top and bottom surfaces.

Tapered surfaces 126 may be provide along the leading end 120 to help facilitate insertion of the implant 110. Additional instrumentation may also be used to help deploy the implant 110 into the disc space. By way of example, the implant installation device shown and described in detail in the commonly owned and copending U.S. patent application Ser. No. 12/378,685, entitled "Implant Installation Assembly and Related Methods," filed on Feb. 17, 2009, the entire contents of which is incorporated by reference herein, may be used to help distract the disc space and deposit the implant therein.

Figure 16:
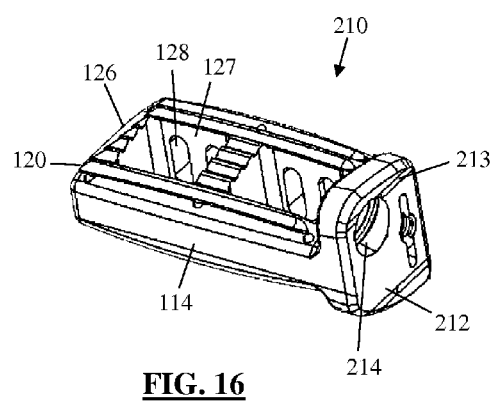
FIGS. 16-17 are posterior-rear perspective and rear views of a hyper-lordotic lateral implant according to another example embodiment.
Figure 17:
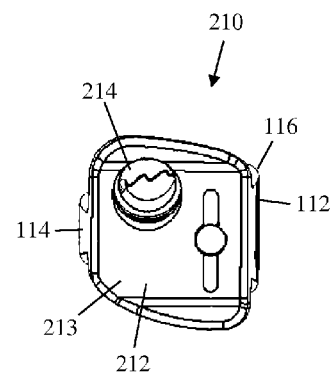

FIGS. 16-17 illustrate an implant 210 according to another example embodiment. The implant 210 shares many similar features with the implant 110 such that like features are numbered alike and repeat discussion in not necessary. The implant 210 differs from the implant 110 in that a trailing side 212 is configured for fixed engagement to one of the adjacent vertebral bodies (i.e. V1 or V2) to supplement the anti-migration features and ensure the hyperlordotic implant is not projected out of the disc space. Specifically, the implant 210 includes a tab 213 extending vertically above the top surface 116 and/or below the bottom surface 118. Tabs 213 facilitate fixation of the implant 210 to the adjacent vertebrae. In the example shown in FIGS. 16-17, the tab 213 extends past both the bottom and top surfaces 118 and 116, respectively. It will be appreciated, however, that the implant 210 may include, without departing from the scope of the present invention and by way of example only, a tab 213 that extends solely in one direction. Additionally, multiple tabs 213 of various sizes and/or shapes may be used throughout a single implant 210 to facilitate implantation or fixation. In the illustrated example, the tab 213 has a single fixation aperture 214 for enabling the engagement of a fixation anchor (not shown) within the vertebral bone to secure the placement of the implant. In use, when the implant 210 is positioned within the disc space, the tab 213 engages the exterior of the upper and lower vertebra and the fixation anchor may be driven into the side of either the upper or lower vertebra. One will appreciate that various locking mechanism may be utilized and positioned over or within the fixation aperture 214 to prevent the fixation anchor from unwanted disengagement with the implant 210. For example, a suitable locking mechanism may be in the form of a canted coil disposed within the fixation aperture 214 or a screw that may be engaged to the trailing side 212 and cover all or a portion of the fixation aperture 214 after the fixation anchor positioned.

Figure 18:
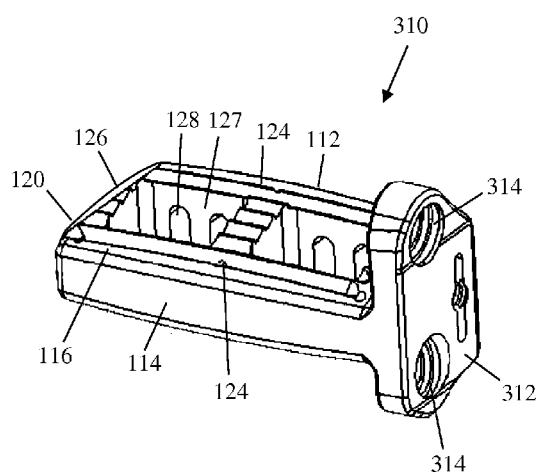
FIGS. 18-19 are posterior-rear perspective and rear views of a hyper-lordotic lateral implant according to still another example embodiment.
Figure 19:
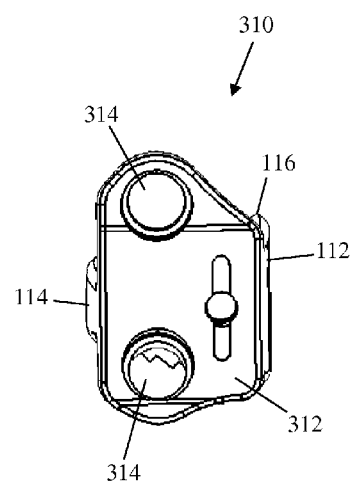

FIGS. 18-19 illustrate an implant 310 according to another example embodiment. The implant 310 shares many similar features with the implants 110 and 110 such that like features are numbered alike and repeat discussion in not necessary. The implant 310 differs from the implant 110 in that a trailing side 312 is configured for fixed engagement to one of the adjacent vertebral bodies (i.e. V1 or V2) to supplement the anti-migration features and ensure the hyperlordotic implant is not projected out of the disc space. Specifically, the implant 310 includes a tab 313 extending vertically above the top surface 116 and/or below the bottom surface 118. Tab 313 facilitates fixation of the implant 310 to the adjacent vertebrae. Tab 313 extends past both the bottom and top surfaces 118 and 116, respectively. It will be appreciated, however, multiple tabs 313 of various sizes and/or shapes may be used throughout a single implant 310 to facilitate implantation or fixation. The implant 310 differs from the implant 210 in that the tab 213 has includes a pair of fixation apertures 214 for enabling the engagement of a pair fixation anchors (not shown) within the vertebral bone to secure the placement of the implant. In use, when the implant 310 is positioned within the disc space, the tab 313 engages the exterior of the upper and lower vertebra and a fixation anchor is driven into the side of each of the upper or lower vertebra. One will appreciate that various locking mechanism may be utilized and positioned over or within the fixation apertures 314 to prevent the fixation anchors from unwanted disengagement with the implant 310. One will also appreciate that single locking mechanism may be used to cover both fixation apertures 314, or, a separate locking mechanism may be used to cover each fixation aperture 314. Again, by way of example, a suitable locking mechanism may be in the form of a canted coil disposed within each fixation aperture 314 or a screw that may be engaged to the trailing side 312 and cover all or a portion of each fixation aperture 314 after the fixation anchors are positioned.

While this invention has been described in terms of a best mode for achieving this invention's objectives, it will be appreciated by those skilled in the art that variations may be accomplished in view of these teachings without deviating from the spirit or scope of the invention. For example, particularly at L5-S1 where the pelvic bone makes a lateral access approach difficult, an antero-lateral approach similar to the approach utilized during appendectomies may be utilized.

What is claimed is:

1. A system comprising:
   a resector including
      a sliding blade having a handle, a hollow shaft defining a central lumen, a head defining a first opening in communication with the central lumen, and a second opening in communication with the central lumen and opposingly positioned from the first opening;
   an implant positionable within an interbody space defined by a first vertebra and a second vertebra, the implant including
      an upper surface to contact the first vertebra when the implant is positioned within the interbody space, a lower surface to contact the second vertebra when the implant is positioned within the interbody space, a distal wall, a proximal wall, an anterior sidewall that faces anteriorly when the implant is positioned within the interbody space, and a posterior sidewall that faces posteriorly when the implant is positioned within the interbody space;
      at least a first fusion aperture extending through the upper surface and lower surface and configured to permit bone growth between the first vertebra and the second vertebra when the implant is positioned within the interbody space; and
      a tab including at least one fixation aperture therethrough configured to receive a fixation anchor, and a locking mechanism configured to prevent disengagement of a fixation anchor from the fixation aperture.

2. The system of claim 1, wherein the implant has a maximum longitudinal length extending from a proximal end of the proximal wall to a distal end of the distal wall, a width extending from the anterior end of the anterior sidewall to the posterior end of the posterior sidewall, the maximum longitudinal length being at least 40 mm, an anterior height extending from the upper surface to the lower surface at the anterior sidewall and a posterior height extending from the upper surface to the lower surface at the posterior sidewall, the anterior height being greater than the posterior height such that the upper and lower surfaces increase in slope from the posterior sidewall to the anterior sidewall forming an angle greater than 20 degrees.

3. The system of claim 1, further comprising a second fusion aperture extending through the upper surface and the lower surface and configured to permit bone growth between the first vertebra and the second vertebra when the implant is positioned within the interbody space.

4. The system of claim 3, wherein the second fusion aperture has a longitudinal aperture length extending generally parallel to a longitudinal length of the implant, and an aperture width extending from the anterior sidewall to the posterior sidewall, wherein the longitudinal aperture length is greater than the aperture width.

5. The system of claim 1, wherein the implant includes anti-migration elements on the upper surface.

6. The system of claim 5, wherein the anti-migration elements comprise a plurality of ridges extending perpendicularly to a longitudinal length of the implant.

7. The system of claim 5, wherein the anti-migration elements comprise a plurality of spike elements.

8. The system of claim 1, further comprising an osteoinductive material positioned within the first fusion aperture.

9. The system of claim 1, wherein the tab extends above the upper surface and is configured to engage an exterior surface of the first vertebra when the implant is positioned within the interbody space.

10. The system of claim 9, wherein the tab extends below the lower surface and is configured to engage an exterior surface of the second vertebra when the implant is positioned within the interbody space.

11. The system of claim 1, wherein the tab includes at least two fixation apertures.

12. The system of claim 1, wherein the fixation anchor is a screw.

13. The system of claim 1, further comprising a tissue retractor configured to travel through the central lumen to create an operative corridor.

14. The system of claim 13, further comprising at least one dilator configured to movably slide with the tissue retractor from a first configuration to a second configuration, wherein the movement to the second configuration enlarges the operative corridor.

15. The system of claim 13, wherein the tissue retractor comprises a barrier.

16. The system of claim 1, further comprising a stimulation electrode configured to deliver an electrical stimulation signal for nerve monitoring.

17. The system of claim 1, wherein the upper surface and the lower surface are each a planar surface.

18. The system of claim 1, wherein the upper surface and the lower surface are each a convex surface.

19. The system of claim 1, further comprising a tissue retractor including a barrier.

20. The system of claim 1, wherein the distal wall, the proximal wall, the anterior sidewall, and the posterior sidewall each comprise radiolucent material.

21. The system of claim 20, wherein the radiolucent material is PEEK.

* * * * *